(12) United States Patent
Singaram et al.

(10) Patent No.: US 6,653,141 B2
(45) Date of Patent: Nov. 25, 2003

(54) POLYHYDROXYL-SUBSTITUTED ORGANIC MOLECULE SENSING METHOD AND DEVICE

(75) Inventors: Bakthan Singaram, Santa Cruz, CA (US); Ritchie A. Wessling, Watsonville, CA (US)

(73) Assignee: The Regents of the University of California, Oakland, CA (US)

( * ) Notice: Subject to any disclaimer, the term of this patent is extended or adjusted under 35 U.S.C. 154(b) by 199 days.

(21) Appl. No.: 09/731,325

(22) Filed: Dec. 5, 2000

(65) Prior Publication Data

US 2002/0106810 A1 Aug. 8, 2002

(51) Int. Cl.$^7$ .............................................. G01N 21/64
(52) U.S. Cl. ...................... 436/95; 436/172; 422/82.08
(58) Field of Search ........................ 436/95, 131, 172; 422/82.07, 82.08, 82.11; 250/458.1, 459.1

(56) References Cited

U.S. PATENT DOCUMENTS

| | | | |
|---|---|---|---|
| 4,659,817 A | 4/1987 | Gallop et al. | 540/541 |
| 4,886,338 A | 12/1989 | Yafuso et al. | 350/96.29 |
| 5,039,491 A | 8/1991 | Saaski et al. | 422/82.05 |
| 5,114,676 A | 5/1992 | Leiner et al. | 422/82.06 |
| 5,137,833 A | 8/1992 | Russell | 436/94 |
| 5,232,858 A | 8/1993 | Wolfbeis et al. | 43/77 |
| 5,242,842 A | 9/1993 | Sundrehagen | 436/536 |
| 5,244,562 A | 9/1993 | Russell | 204/418 |
| 5,246,867 A * | 9/1993 | Lakowicz et al. | 422/82.07 |
| 5,342,789 A * | 8/1994 | Chick et al. | 424/9.6 |
| 5,466,798 A | 11/1995 | Singaram et al. | 540/541 |
| 5,503,770 A | 4/1996 | James et al. | 252/301.16 |
| 5,512,246 A | 4/1996 | Russell et al. | 422/57 |
| 5,517,313 A | 5/1996 | Colvin, Jr. et al. | 356/417 |
| 5,631,364 A | 5/1997 | Sundrehagen et al. | 540/128 |
| 5,763,238 A | 6/1998 | James et al. | 436/72 |
| 5,777,060 A | 7/1998 | Van Antwerp et al. | 528/28 |
| 5,786,439 A | 7/1998 | Van Antwerp et al. | 528/77 |
| 5,852,126 A | 12/1998 | Barnard et al. | 525/326.3 |
| 5,882,494 A | 3/1999 | Van Antwerp | 204/403 |
| 5,894,351 A | 4/1999 | Colvin, Jr. et al. | 356/417 |
| 5,922,612 A | 7/1999 | Alder et al. | 436/163 |
| 6,002,954 A | 12/1999 | Van Antwerp et al. | 600/317 |
| 6,011,984 A * | 1/2000 | Van Antwerp et al. | 600/310 |
| 6,063,637 A | 5/2000 | Arnold et al. | 436/94 |
| 6,344,360 B1 * | 2/2002 | Colvin et al. | 436/166 |
| 6,387,672 B1 * | 5/2002 | Arimori et al. | 252/301.16 |

FOREIGN PATENT DOCUMENTS

| | | | |
|---|---|---|---|
| WO | WO 92/08722 | 5/1992 | C07F/5/02 |
| WO | WO 97/19188 | 5/1997 | C12Q/1/100 |
| WO | WO 01/74968 A2 | 10/2001 | C09K/11/00 |

OTHER PUBLICATIONS

P.D. Hale, et al, Investigation of Viologen Derivatives Electron–Transfer Mediators in Amperometric Glucose Sensors, Analytica Chimica Acta, vol. 248:155–161, (1991).

D. E. Smith, et al., Entropy of Associatin of Methane in Water: A New Molecular Dynamics Computer Simulation, J. Am. Chem. Soc., 114:5875–5876 (1992).

A. B. Kotlyar, et al., The Dynamics of Proton Transfer at the C Side of the Mitochondrial Membrane: Picosecond and Micosecond Measurements, Biochemistry, 33:873–879 (1994).

E.T.B. Al–Takrity, Synthesis of Poly(Methacrylic Acid) Bearing Fluorescent and Fluorescence–Quenching Groups, Euro. Polym. J., 31(4):383–385 (1995).

H. Murakami, et al., Sugar Sensing Utilizing Aggregation Properties of Boronic–Acid–Appended Porphyrins and Metalloporphyrins, J. Chem. Soc. Perkin Trans 2:975–981 (1994).

H. Shinmori, et al., Spectroscopic Sugar Sensing by a Stilbene derivative with Push (Me2N–)–Pull((HO)2B–)–Type Substituents, Tetrahedron, 51(7):1893–1902 (1995).

H. Murakami, et al., Sugar Sensing Utilizing Aggregation Properties of Boronic–Acid–Appended Porphyrins, Tetrahedron Letters, 34(39):6273–6276 (1993).

T. D. James, et al., A Glucose–Selective Molecular Fluorescence Sensor, Angew. Chem. Int. Ed. Engl. 33(21):2207–2209 (1994).

Shinkai, et al., by Trans–3,3–Stilbenediboronic Acid: Rigidification of the Stilbene Skeleton Upon Formation of a . . . , J. Chem Soc., Chem. Commun., 1621–1622 (1994).

G. Deng, et al., Allosteric Interaction of Metal Ions with Saccharides in a Crowned Diboronic Acid, J. Am. Chem. Soc., 116:4567–4572 (1994).

K.R.A. Sandanayake, et al., Novel Molecular Sensors for Saccharides Based on the Interaction of Boronic Acid and Amines: Saccharide Sensing in Neutral Water, J. Chem. Soc., Chem. Commun., 1083–1084 (1994).

T. D. James, et al., Novel Photinduced Electron–Transfer Sensor for Saccharides Based on the Interaction of Boronic Acid and Amines, J. Chem. Soc., Chem. Commun., 477–478 (1994).

(List continued on next page.)

Primary Examiner—Jeffery Snay
(74) Attorney, Agent, or Firm—Peters, Verny, Jones & Schmitt, LLP,; Howard M. Myers

(57) ABSTRACT

The present invention concerns an improved optical method and optical sensing device for determining the levels of polyhydroxyl-substituted organic molecules in vitro in aqueous or organic media. Specifically, a dye is combined with an conjugated nitrogen-containing aromatic heterocyclic aromatic boronic acid-substituted bis-onium compound in the presence of a sugar, such as fructose or glucose. The viologens are preferred as the aromatic conjugated nitrogen containing boronic acid substituted compounds. The method is useful to determine sugar levels in fermentation and process streams.

18 Claims, 10 Drawing Sheets

OTHER PUBLICATIONS

K.R.A. Samankumara Sandanayake, et al., Molecular Fluorescence Sensor for Saccharides Based on Amino Coumarin, Chemistry Letters, 139–140 (1995).

Masayuki Takeuchi, et al., Fluorescence and CD Spectroscopic Sugar Sensing by a Cyanine–appended Diboronic Acid Probe, Tetrahedron, 52(4):1195–1204 (1996).

Hibaru Suenaga, et al., Screening of Boronic Acids for Strong Inhibition of the Hydrolytic Activity of alpha–chymotrysin and for Sugar Sensing Associated with a Large Fluorescence Change, Pure & Appl. Chem., 68(11):2179–2186 (1996).

Stephen G. Schulman, et al., Dependent of the Fluorescence of Immobilized 1–hydroxypyrene–3,6,8–Trisulfonate on Solution pH; Extension of the Range of Applicability of a pH Fluoresensor, Analytica Chimica Acta, 304, 165–170 (1995).

Hibaru Suenaga, et al., Screening of Fluorescent Boronic Acids for Sugar Sensing Which Show a Large Fluorescence Change, Tetrahedron Letters, 36(27):4825–4828 (1995).

Tony D. James, et al., Novel Fluorescence Sensor for Small Saccharides, Chem. Commun., 71–72 (1997).

Fabbrizzi, et al, Fluorescent Sensor Imidazole and Histidine, Chem. Commun., 581–582 (1997).

K.R.A. Samankura Sandanayaki, et al., Two Dimensional Photoinduced Electron Transfer (PET) Fluorescence Sensor, Chemistry Letters, 503–504 (1995).

Jens Chr. Norrild, et al., Evidence for Mono–and Bisdenate Boronate Complexes of Glucose in the Furanose Form. Application of $^1$Jc–c Coupling Constants as a Structural Probe, J. Am. Chem. Soc., 117:1479–1484 (1995).

Fumio Ohseto, et al., Allosteric Communication between the Metal–binding Lower Rim and the Sugar–binding Upper Rim on a Calix[4]crown Platform, Tetrahedron Letters, 36(38):6911–6914 (1995).

Kazunori Kataoka, et al., Novel Sensing System for Glucose Based on the Complex Formation Between Phenylborate and Fluorescent Diol Compounds, J. Compounds, J. Biochem., 117:1145–1147 (1995).

Tony D. James, et al., Novel Saccharide–Photoinduced Electron Transfer Sensors Based on the Interaction of Boronic Acid and Amine, J. Am. Chem. Soc., 117:8982–8987 (1995).

Patrick Linnane, et al., The Synthesis and Properties of Calixarene–based Sugar Bowl, J. Chem. Soc., Chem. Commun., 1997–1998 (1995).

Susumu Arimori, et al., Sugar–Sensing by Chiral Orientation of Dimeric Boronic–Acid–Appended Porphyrins Which Show Selectivity for Glucose and Xylose, Chemistry Letters, 77–78 (1996).

Kazuaki Nakashima, et al., Diaza–18–crown–6–based Sugar Receptor Bearing Two Boronic Acids. Possible Communication Between Bound Sugars and Metal Cations, Chemistry Letters, 443–444 (1995).

Alexander B. Kotlyar, et al., Fast Redox Perturbation of Aqueous Solution by Photoexcitation of Pyranine, Photochemistry and Photobiology, 63(4):448–454 (1997).

Masayuki Takeuchi, et al., Chiral Sugar Recognition by a Diboronic–Acid–Appended Binaphthyl Derivative Through Rigidification Effect, Tetrahedron, 53(25):8335–8348 (1997).

Aiichiro Ori et al., Electrochemical Detection of Saccharides by the Redox Cycle of a Chiral Ferrocenylboronic Acid Derivative: A Novel Method for Sugar Sensing, Chem., Soc., Chem. Commun., 1771–1774 (1995).

Masayuki Takeuchi, et al., A Novel Sugar Sensing System Designed with a Cooperative Action of a Boronic–Acid–Appended Zinc Porphyrin and a 3–Pyridylbornoic Acid Axial Ligand, Bull. Chem. Soc., Jpn., 70:699–705 (1997).

Hideyuki Shinmori, et al., Spectroscopic Detection of Diols and Sugars by a Coulour Change in Boronic Acid–Appended Spirobenzopyrans, J. Chem. Soc., Perkins Trans. 2, 1–3 (1996).

Kenichi Nakashima, et al., Fluorescence Quenching of 1–Pyrenemethanol by Methylviologen in Polystyrene Latex Dispersions, Photochemistry and Photobiology, 64(2):296–302 (1996)

Rolf Uggla, et al., Boronic Acids As Molecular Sensors NBO Analysis and 13C Chemical Shifts as Tools for Evaluation of DFT Geometry Optimization of Complexes of Diphenylmethane, 3,3'–Diboronic Acids and Glucose, Tetrahedron Assymetry, 7(6):1741–1748 (1996).

Seiji Shinkai, et al., Molecular Design of Artificial Sugar Sensing Systems, Trends in Analytical Chemistry, 15(5);188–194 (1996).

U.E. Spichiger, Biomimetic Recognition Elements for Sensor Applications, Frontier in Biosciences: Fundamental Aspects, 27–48 (1997).

Mauricio S. Matos, et al., Spectroscopic and Kinetic Study of the Molecular Association Between Pyrene and Benzyl Viologen, Spectrochimica Acta, Part A, 54:1857–1867 (1998).

Hann Eggert, et al., A New Glucose–Selective Fluorescent Bisboronic Acid, First Report of Strong alpha–Furanose Complexation in Aqueous Solution of Physiological pH, J. Org. Chem., 64:3846–3852 (1999).

Ryan J. Russell, at al., A Flourescence–Based Glusose Biosensor Using Concanavalin A and Dextran Encapsulated in a Poly(ethylene gylcol) Hydrogel, Anla., Chem., 71:3126–3132 (1999).

B. Appleton, et al., Detection of Total Sugar Concentration Using Photoinduced Electron Transfer Materials: Development of Operationally Stable, Reusable Optical Sensors, Sensors and Actuators B, 65:302–304 (2000).

George S. Wilson, et al., Enzyme–Based Biosensors for In Vivo Measurements, Chem. Rev., 100:2693–2704 (2000).

Bruce W. Bode, et al., Continuous Glucose Monitoring Used to Adjust Diabetes Therapy Improves Glycosylated Hemoglobin: A Pilot Study, Diabetes Research and Clinical Practice, 46:183–190 (1999).

Liaohai Chen, et al., Highly Sensitive Biological and Chemical Sensors Based on Reversible Fluorescence Quenching in a Conjugated Polymer, PNAS, 96(22):12287–12292, (Oct. 26, 1999).

Peter S. Heeger, et al., Making Sense of Polymer–Based Biosensors, PNAS, (96)22):12219–12221, (Oct. 26, 1999).

E. B. deBorba, et al., Photophysical and Photochemical Properties of Pyranine/Methyl Viologen complexes in Solution and in Supramolecular Aggregates: A Switchable Complex, Langmuir, 16:5900–5907 (2000).

Liat Genoser, et al., Ultrafast Direct Photoacid–Based Reaction, J. Phys. Chem. A, 104:6689–6698 (2000).

Roger J. McNichols, et al., Optical Glucose Sensing in Biological Fluids: An Overview, Journal of Biomedical Optics, 5(1):5–16 (Jan. 2000).

Jian Wang, et al., Photoluminiscence of Water–Soluble Conjugated Polymers: Origin of Enhanced Quenching by Charge Transfer, Macromolecules, 33:5153–5158 (2000).

Abstracts, American Chemical Society Division of Organic Chemistry, 220th ACS Meeting, Wahington DC, Aug. 20–24, 2000, #43, #237, #245 and #254.

The Dangerous Toll of Diabetes, American Diabetes Association (2000).

Anthony P. F. Turner, et al., In Vitro Diagnostics in Diabetes: Meeting the Challenge, Clinical Chemistry, 45:9, 1596–1601 (1999).

* cited by examiner

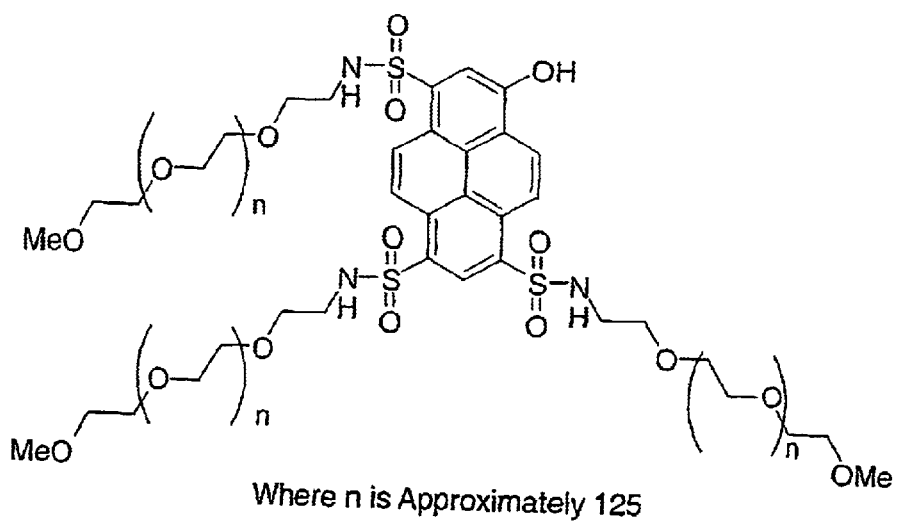
FIG._1A
Where n is Approximately 125
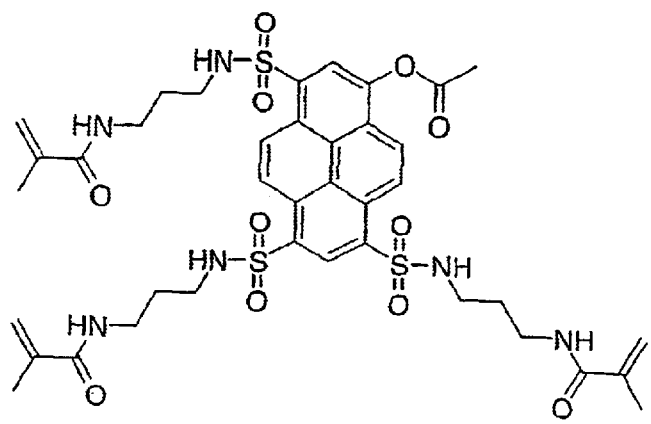
FIG._1B

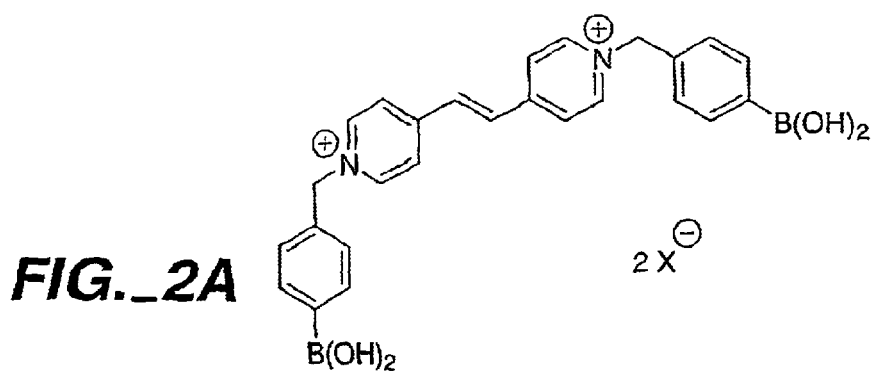
FIG._2A
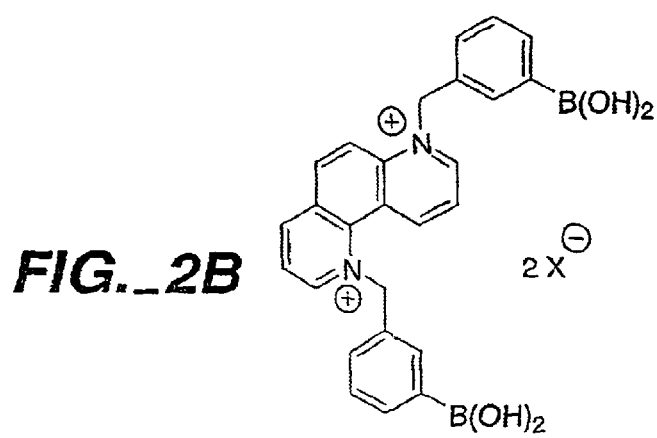
FIG._2B
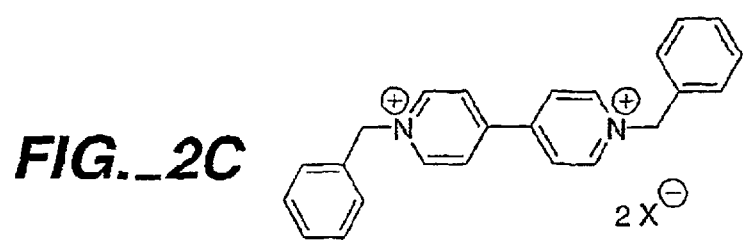
FIG._2C
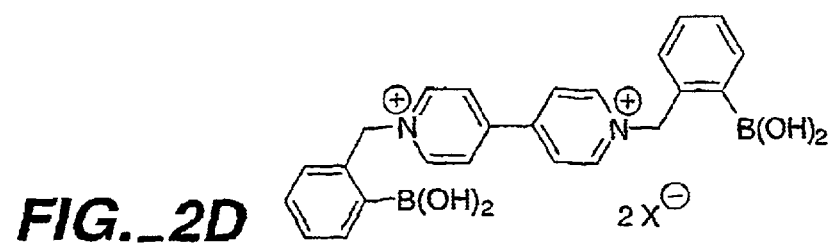
FIG._2D

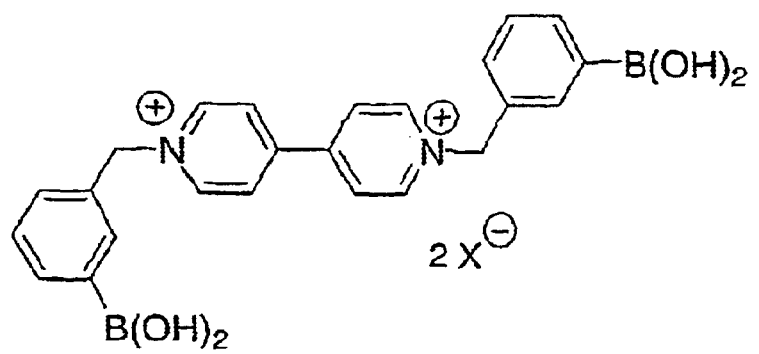
FIG._2E
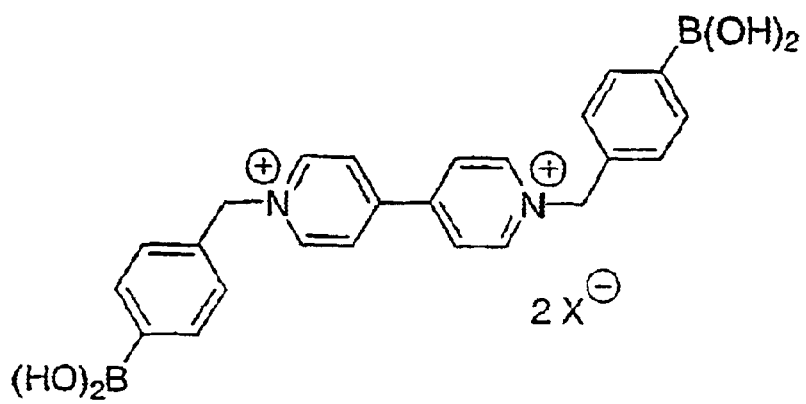
FIG._2F

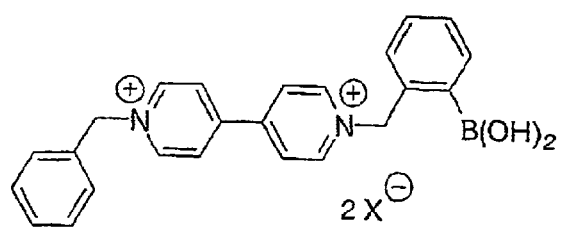
*FIG._3A*
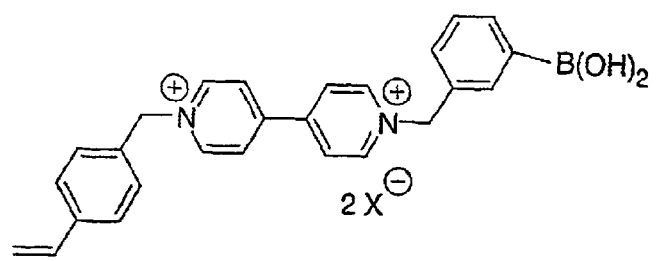
*FIG._3B*
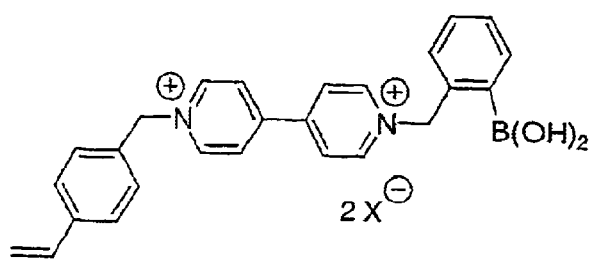
*FIG._3C*
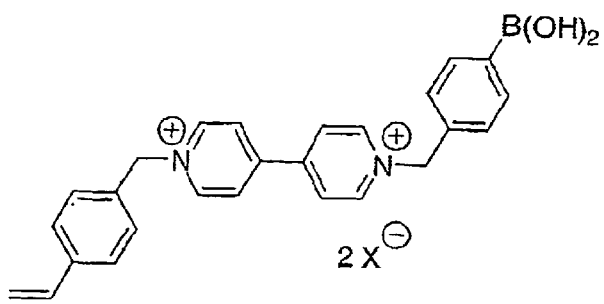
*FIG._3D*
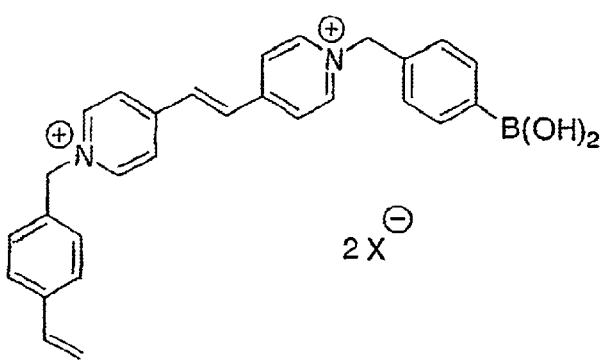
*FIG._3E*

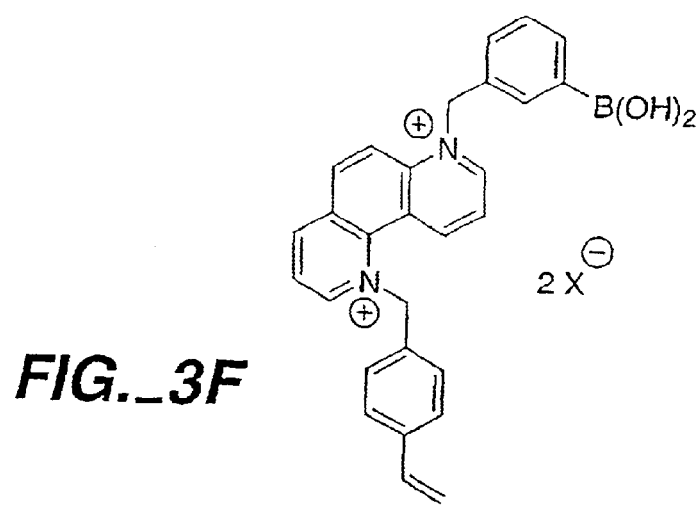
FIG._3F

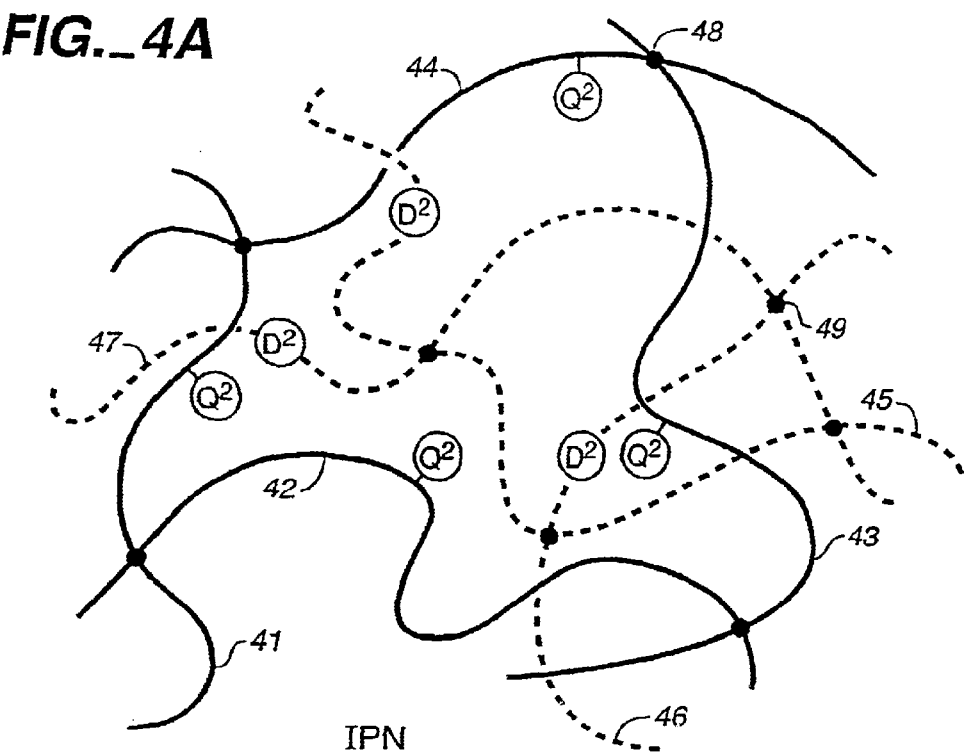
FIG._4A
IPN
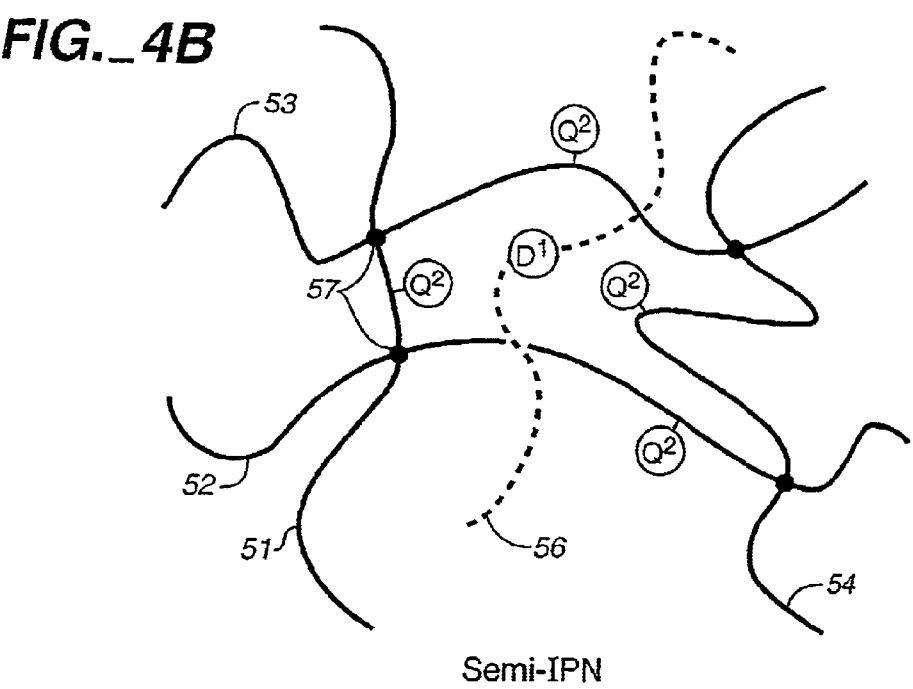
FIG._4B
Semi-IPN

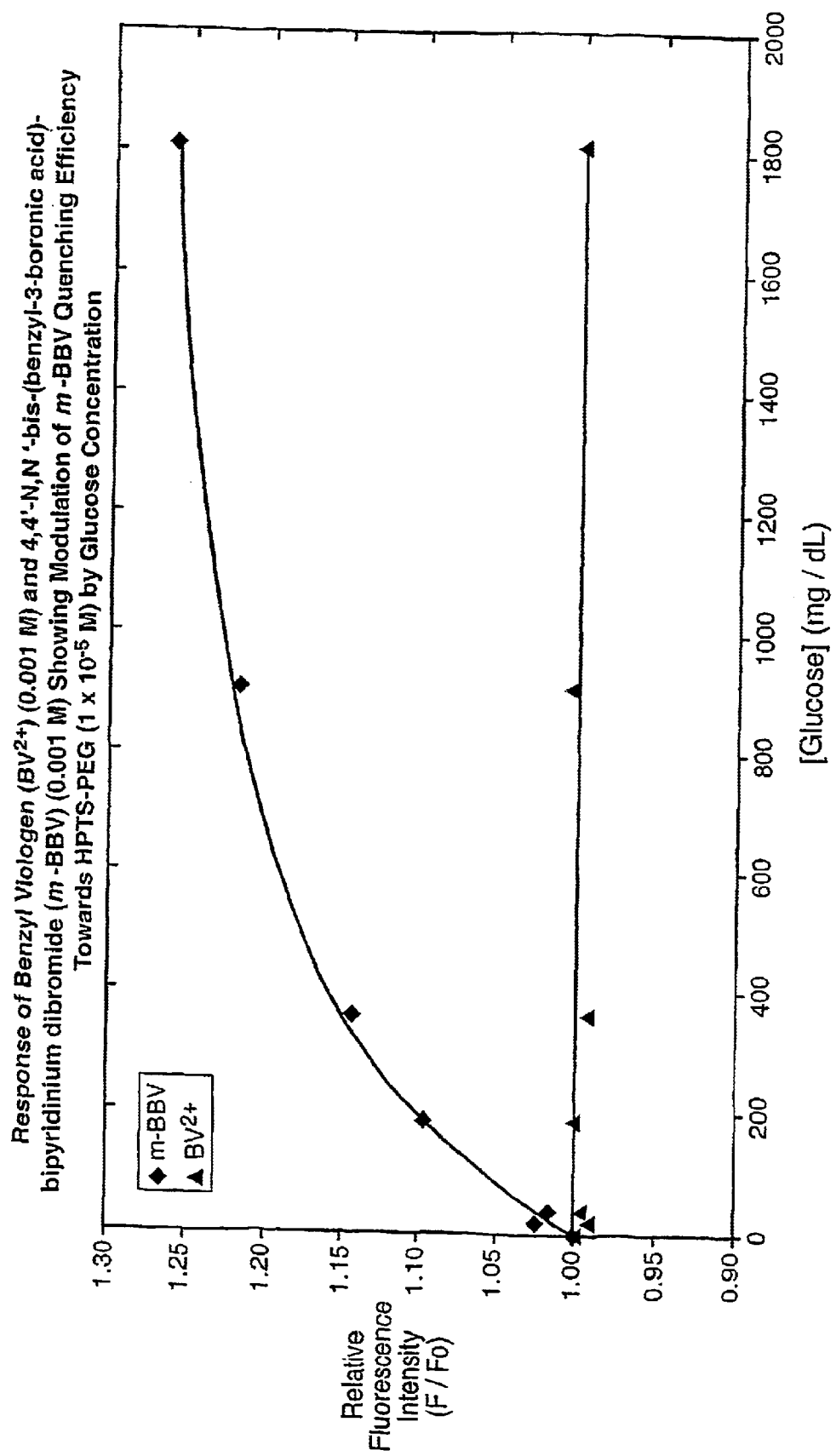

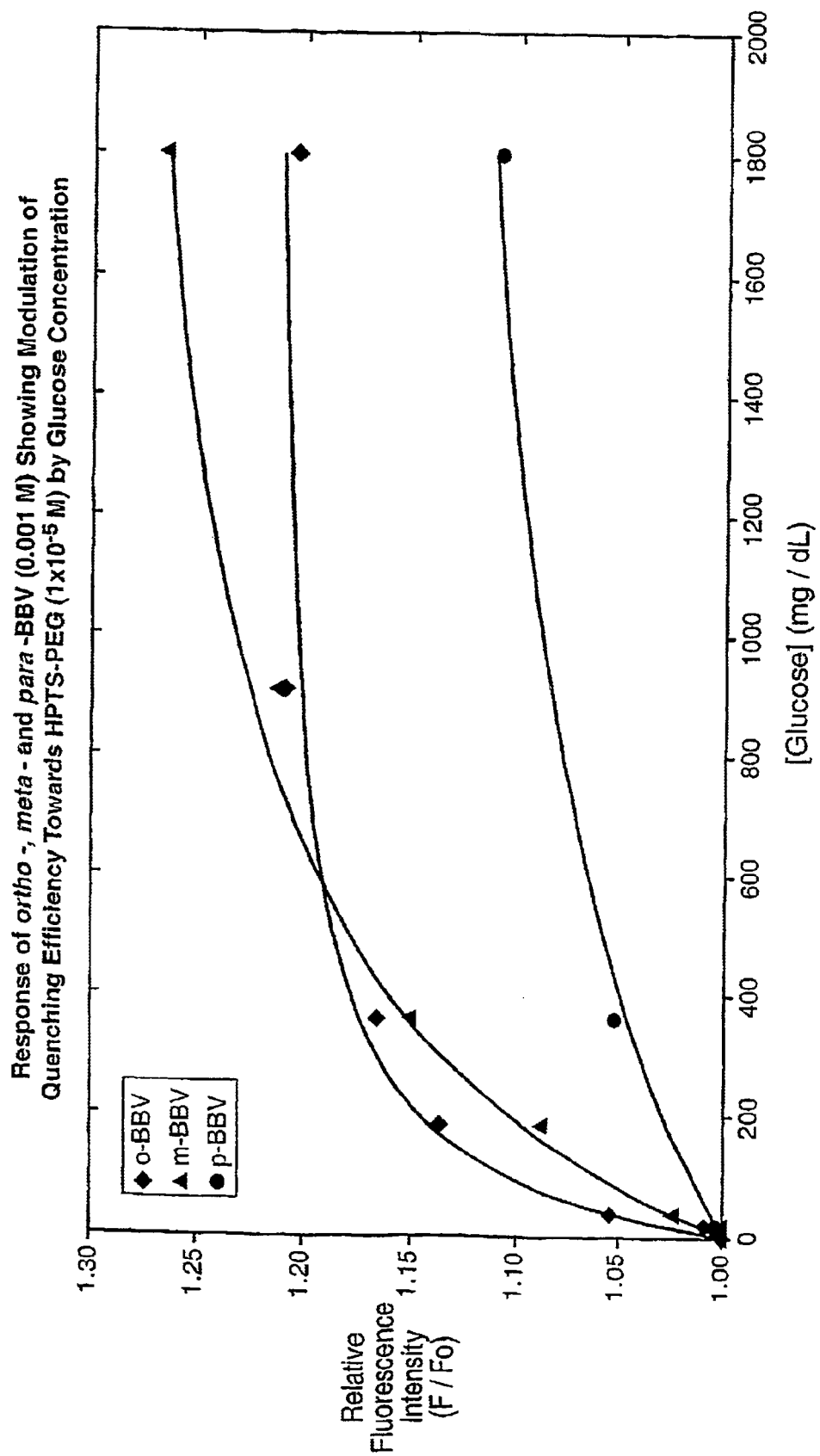
FIG._6

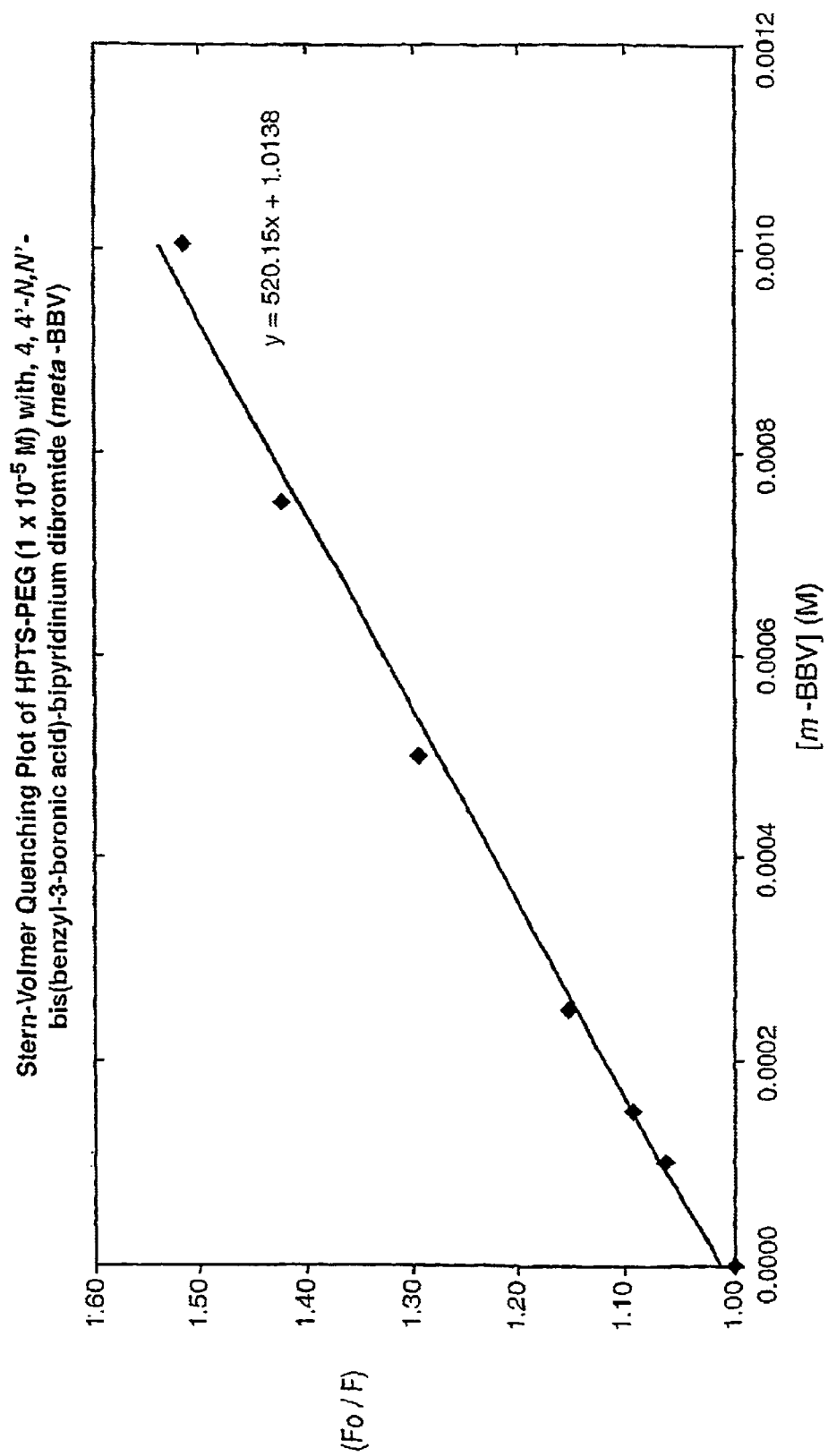

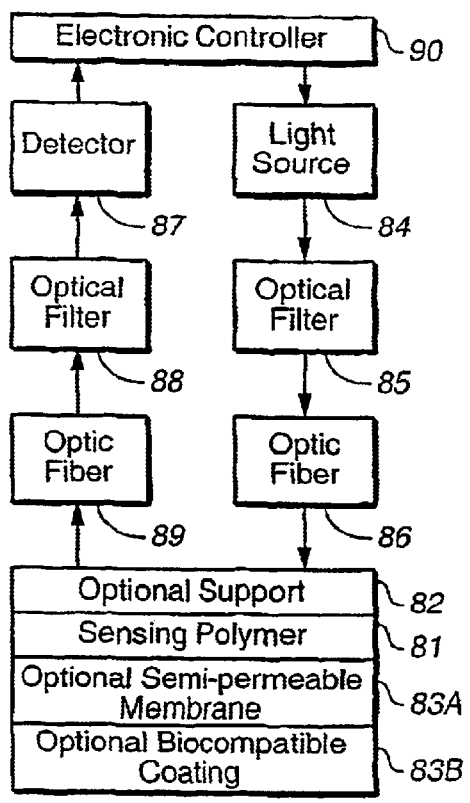
FIG._8
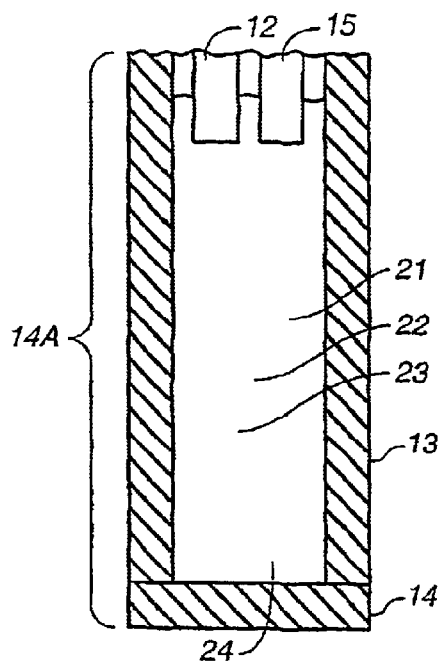
FIG._10
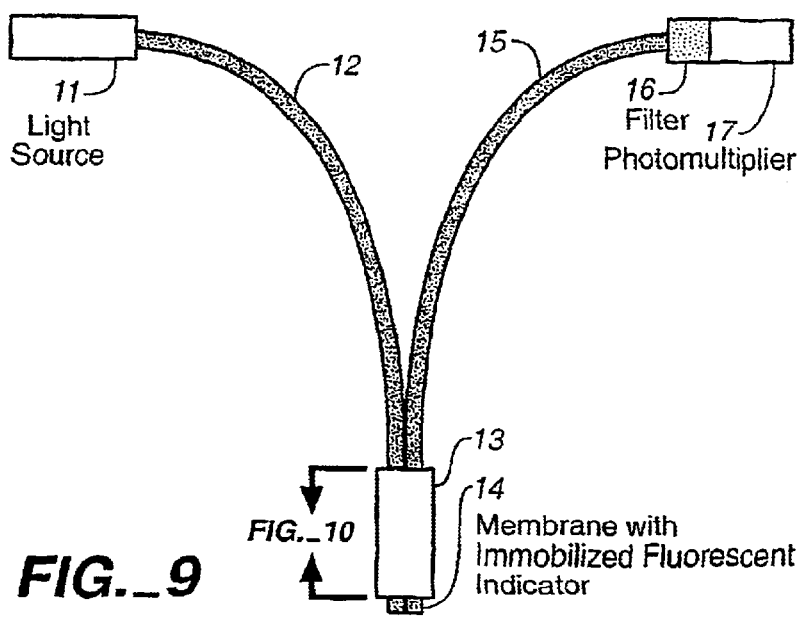
FIG._9

POLYHYDROXYL-SUBSTITUTED ORGANIC MOLECULE SENSING METHOD AND DEVICE

BACKGROUND OF THE INVENTION

1. Field of the Invention

This invention relates to an improved optical method and sensor for polyhydroxy-substituted organic molecules that measure the concentration of these molecules in aqueous or organic media. In particular, the method and sensor monitor the concentration of sugars, i.e. glucose or fructose, in aqueous solution in vitro. The determination of glucose in samples of body fluid in vitro is of particular importance. Some of the novel components of the optical method and device are also considered to be inventions in their own right.

2. Description of Related Art

There has been an ongoing effort over many years to use fluorescence techniques to measure polyhydroxyl compound (e.g. glucose) concentrations in body fluids. Although the term "glucose" is used herein below, it is to be understood that the concentration of most polyhydroxyl-containing organic compounds (carbohydrates, 1,2-diols, 1,3-diols and the like) in a solution are capable of being determined. But in spite of the intense effort, no practical system has been developed and commercialized. Several attempts have been made to detect glucose by fluorescence using dyes to which a boronic acid group has been attached. Boronic acids are known to bind sugars reversibly. When the boronic acid functional dye binds to a sugar, the properties of the dye are affected. These changes have been used in the past to measure sugar concentration.

One use of this approach to a glucose sensor was reported by Russell, U.S. Pat. No. 5,137,833 (See also Russell & Zepp, U.S. Pat. No. 5,512,246) which disclosed the use of a boronic acid functionalized dye that binds to glucose and generates a signal dependent on glucose concentration. James et al, U.S. Pat. No. 5,503,770,used the same principle but combined a fluorescent dye, an amine quenching functionality, and a boronic acid in a single complex moiety, the fluorescence emission from which varies with extent of glucose binding. Van Antwerp et al, U.S. Pat. Nos. 6,002,954 and 6,011,984 combined features of the previously cited references and also taught fabrication of a device that is purported to be implantable.

Patents of interest include but are not limited to:
Russell, U.S. Pat. No. 5,137,833 (1992)
James et al, U.S. Pat. No. 5,503,770 (1996)
Russell & Zepp, U.S. Pat. No. 5,512,246 (1996)
Van Antwerp et al, U.S. Pat. No. 6,002,954 (1999)
Van Antwerp and Mastrototaro, U.S. Pat. No. 6,011,984 (2000)
Related U.S. patents of interest include:
Wolfbeis et al, U.S. Pat. No. 4,586,518 (1986)
Gallop & Paz, U.S. Pat. No. 4,659,817 (1989)
Yafuso & Hui, U.S. Pat. No. 4,798,738 (1989)
Yafaso & Hui, U.S. Pat. No. 4,886,338 (1989)
Saaski et al, U.S. Pat. No. 5,039,491 (1991)
Lanier et al, U.S. Pat. No. 5,114,676 (1992)
Wolfbeis et al, U.S. Pat. No. 5,232,858 (1993)
Colvin, U.S. Pat. No. 5,517,313 (1996)
Sundrehagen et al, U.S. Pat. No. 5,631,364 (1997)
James et al, U.S. Pat. No. 5,763,238 (1998)
Siegmund et al, U.S. Pat. No. 5,711,915 (1998)
Barnard & Rouilly, U.S. Pat. No. 5,852,126 (1998)
Colvin, U.S. Pat. No. 5,894,351 (1999)
Alder et al, U.S. Pat. No. 5,922,612 (1999)
Arnold et al, U.S. Pat. No. 6,063,637 (2000)
Song et al, U.S. Pat. No. 6,046,312 (2000)
Kimball et al, U.S. Pat. No. 6,139,799 (2000)
Chick et al, U.S. Pat. No. 6,040,194 (2000)
Related articles and publications of interest include:
Yoon & Czarnik, *J. Amer. Chem. Soc.* (1992) 114, 5874–5875
James, Linnane, & Shinkai, *Chem. Commun.* (1996), 281–288
Suenaga et al, *Tetrahedron Letters* (1995), 36, 4825–4828
Eggert et al, *J.Org.Chem.* (1999), 64, 3846–3852
Wolfbeis et al, *Analytica Chimica Acta* (1995), 304, 165–170
Wang et al, *Organic Letters* (1999), 1, 1209–1212
Chen et al, *Proc. Nat. Acad. Sci.* (1999), 96, 12287–12292
P. D. Hale et al, *Analytica Chimica Acta* (1999), 248, 155–161
A. E. Colvin, Jr. et al, *Johns Hopkins Technical Digest*, Vol. 12, #17, p.378 (1996)
Murakami et al, *Chem. Letters (Japan)* (2000), (8), p. 940–941.
References of a general nature include:
A. W. Czarnik (ed), *Fluorescent Chemosensors for Ion and Molecule Recognition* ACS Washington, D.C. 1992.
F. W. Scheller et al (eds), *Frontiers in Biosensorics I Fundamental Aspects*, Birkhaüser Vertag, Basel 1997.
J. R. Lakowicz, *Principles of Fluorescence Spectroscopy*, $2^{nd}$ed. Kluwer Academics/Plenum Publishers, New York, N.Y. (1999).
Haugland, R. P. *Handbook of Fluorescent Probes and Research Chemicals* $6^{th}$ ed. Molecular Probes Inc., Eugene, Oreg. (1996).

All patents, articles, references, standards and the like cited in this application are incorporated herein by reference in their entirety.

All of these prior art sensors are deficient in one or more aspects, such as operability under physiological conditions, stability of operation, simplicity of design, reliability, and sensitivity. The present invention overcomes these deficiencies.

SUMMARY OF THE INVENTION

This present invention concerns an optical method and an optical device for determining in vitro the concentrations of polyhydroxyl compounds, especially sugars such as glucose or fructose, in aqueous and/or organic media. These compounds, the analytes, are in a system with a fluorescence sensing device comprised of a light source, a detector, a fluorophore (fluorescent dye), a quencher and an optional polymer matrix. Some components may be inventions in their own right. When excited by light of appropriate wavelength, the fluorophore emits light (fluoresces). The intensity of the light is dependent or, the extent of quenching. The fluorophore and quencher are preferably independent entities, optionally they are immobilized in or covalently attached to a polymeric matrix which is permeable to or in contact with the compounds of interest to be detected and quantified.

In one aspect, the present invention comprises a class of fluorescence quenching compounds that are responsive to the presence of polyhydroxyl compounds such as glucose in aqueous or organic media optionally at or near physiological pH. In other words, the quenching efficiency is controlled by the concentration of these compounds in the medium. The quencher is comprised of a viologen substituted with at least one boronic acid group as a discrete molecule, or wherein the adduct is optionally immobilized or covalently bonded to a polymer. The quencher, dye and an optional polymer may also be covalently bonded to each other.

The combination of boronic acid and viologen, and the resultant effect on viologen properties are important embodiments of the present invention.

In another aspect, the present invention is a class of polymeric fluorescent dyes which are susceptible to quenching by the viologen/boronic acid adduct. Useful dyes include pyranine derivatives (e.g. hydroxypyrene trisulfonamide derivatives and the like (See FIGS. 1A and 1B).

In one embodiment, the dye is comprised of a hydroxypyrene trisulfonamide moiety bonded to a polymer. Converting sulfonic acid groups to sulfonamide groups shifts the pKa of pyranine into a range more suitable for measurement at physiological pH. These derivatives are typically prepared by reacting a trisulfonyl chloride intermediate with 1) a polyamine, 2) an amine functional ethylenically unsaturated monomer which adduct is subsequently polymerized, 3) or an amine functional polymer. Preferably, the dye is a fully substituted trisulfonamide containing no residual sulfonic acid groups.

In another aspect, the present invention is a composite water or organic solvent-compatible polymer matrix, preferably a hydrogel, which comprises the dye and quencher moieties. The matrix is a water- or organic liquid-swellable copolymer, preferably crosslinked, to which the dye and quencher moieties are covalently bonded. More preferably, the matrix is an interpenetrating polymer network (IPN) with the dye incorporated in one polymer network and the quencher in the other polymer. Most preferably, the matrix is a semi-IPN wherein the dye component is a high molecular weight water- or organic-soluble or dispersible polymer trapped in a crosslinked network comprised of quencher monomer and suitable hydrophilic comonomers. Optionally, the quencher may be in the water or organic liquid-compatible or dispersible component and the dye within the network. Further both dye and quencher may be separately incorporated in water- or organic-soluble or dispersible polymers wherein dye and quencher are both trapped in an inert polymer matrix. Optionally, the components are separated from the analyte solution by a membrane which is impermeable to the sensing components, but permeable to the analyte. Optionally, the matrix is molecularly imprinted to favor association between dye and quencher, and to enhance selectivity for specific sugars, e.g. glucose, over other polyhydroxy compounds (such as fructose).

In another embodiment, the present invention concerns a device for measuring the concentration of glucose in vitro by means of an optical sensor. The specific device is comprised of a visible or ultraviolet light source, e.g. a blue LED light source, a photodetector, a light conduit such as an optical fiber assembly, and a water- or solvent-insoluble polymer matrix comprised of a fluorophore susceptible to quenching by a viologen, a viologen/boronic acid quencher, and a glucose permeable polymer, wherein the matrix is in contact with said conduit and with the medium containing the analyte.

In another embodiment the present invention relates to an optical method for the in vitro detection between about 300 and 800 nm of polyhydroxyl-substituted organic molecules as the analyte in an analyte solution selected from an aqueous liquid, an organic liquid or combinations thereof at pH of about 5 to 9, which method comprises:

A. obtaining a fluorophore dye D, which is compatible with the analyte solution, wherein D is selected from:

(a) $D^1$ which is a fluorophore dye having the properties of
  i. A fluorophore,
  ii. An excitation in the range greater than 300 nm and less than 800 nm,
  iii. Resistant to photobleaching under the conditions of analysis,
  iv. A Stokes shift of about or greater than 30 nm,
  v. Compatibility with said analyte solution, and wherein
  vi. said Dye $D^1$ is quenched by methyl viologen to produce an experimentally determined apparent Stern-Volmer quenching constant (Ksv) greater than or equal to 50,
  wherein the fluorophore dye $D^1$ is a discrete soluble compound or is a pendant group or a chain unit in a water-soluble or dispersible or organic liquid soluble or dispersible polymer, and said polymer optionally is non-covalently immobilized within an insoluble polymer matrix $M^1$; and wherein said polymer matrix $M^1$ is permeable to or in contact with said analyte solution;

(b) $D^2$ is a fluorophore dye having the properties of
  i. A fluorophore,
  ii. An excitation in the range greater than 300 nm and less than 800 nm,
  iii. A Stokes shift of about or greater than 30 nm,
  iv. Resistant to photobleaching under the conditions of analysis,
  v. Compatibility in the analyte solution, and wherein said
  vi. Dye $D^2$ is quenched by methyl viologen to produce an apparent Stern-Volmer quenching constant (Ksv) greater than or equal to 50, wherein $D^2$ is covalently bonded to an insoluble polymer matrix wherein said polymer matrix $M^1$ is permeable to or in contact with said analyte; wherein said fluorophore dye $D^2$ is a pendant group or is a part of the structure: $M^1$—$L^1$—$D^2$
  wherein:
    $M^1$ is said polymer matrix,
    $L^1$ is a hydrolytically stable divalent linking group selected from a direct bond or a lower alkylene having 1 to 8 carbon atoms, optionally terminated with or including one or more divalent connecting groups selected from sulfonamide, amide, ester, ether, sulfide, sulfone, phenylene, urethane, urea, thiourea or amine, and
    $D^2$ is said fluorophore dye which is covalently bonded to said polymer matrix $M^1$ with the proviso that $D^2$ being polyfunctional is covalently bonded to said matrix $M^1$ at one, two or three sites, B. Combining with an analyte solution-compatible boronic acid-containing quencher moiety Q, wherein Q is a conjugated nitrogen-containing heterocyclic aromatic bisonium salt selected from:
  (i) $Q^1$ which is a discrete soluble compound or is a pendant group or chain unit in a water-soluble or dispersible-polymer or an organic-soluble or dispersible polymer and said polymer optionally is non-covalently associated with the optional polymer matrix $M^1$ when present and immobilized within said polymer matrix $M^1$, wherein $Q^1$ is a compound having the properties of: compatibility in said analyte solution, produces a detectable change in the emission of the dye in the presence of said analyte, or (ii) $Q^2$ which is a structure having the properties of: compatibility in said analyte solution produces a detectable change in the emission of the dye in the presence of said analyte, wherein $Q^2$ is covalently bonded by a linking group $L^2$ to $M^1$ or to a second insoluble polymer matrix $M^2$ producing $M^2$—$L^2$—$Q^2$, wherein $L^2$ is selected from a direct bond and a lower alkylene having 1 to 8 carbon atoms, optionally terminated with or including one or more divalent connecting groups selected from sulfonamide, amide, ester, ether, sulfide, sulfone, phenylene, urethane, urea, thiourea or amine, wherein said quencher $Q^1$ or $Q^2$ is mixed at a molecular level with said fluorophore dye $D^1$ or $D^2$ with the proviso that $Q^2$ being polyfunctional is covalently bonded to said matrix $M^1$ or $M^2$ at one or two sites, and C. contacting a test solution of analyte, a dye and a quencher in vitro with an excitation light source coupled with a detector;

D. producing a detectable and quantifiable signal in the range of about 300 nm to 800 nm; and E. determining the concentration of said polyhydroxyl-substituted analyte in said aqueous liquid, organic liquid or combinations thereof.

In another aspect of the method, the Dye $D^1$ is selected from either the group consisting of:

pyranine;

pyranine derivatives having the structure of:

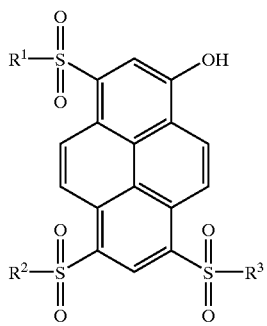

where $R^1$, $R^2$ and $R^3$ are same or different and wherein $R^1$, $R^2$ and $R^3$ are each selected from: —OH, —N($R^4$)$R^5$, wherein $R^4$ is selected from —H, —CH$_3$, and —CH$_2$CH$_2$OH, and $R^5$ is selected from —CH$_2$—CH$_2$(—O—CH$_2$—CH$_2$)$_n$—$X^1$ or $R^6X^1$, wherein $X^1$ is selected from —OH, —OCH$_3$, —CO$_2$H, —CONH$_2$, —SO$_3$H, or —NH$_2$, and $R^6$ is a lower alkylene or hydroxyalkylene having 2 to 6 carbon atoms;

n is about 2 to 10,000, preferably about 2 to 1000, more preferably 2 to 200; coumarin 343; eosin Y; fluorescein; 4,4-difluoro-1,3,5,7,8-pentamethyl-4-bora-3a,4a-diaza-s-indacene-2,6-disulfonic acid, disodium salt (Molecular Probes D-3238); Lucifer Yellow Iodoacetamide dipotassium salt Molecular Probes L-1338); fluorescein-5-(and-6)-sulfonic acid, trisodium salt (Molecular Probes F-1130); and the like.

In another aspect of the method, the Dye $D^2$ is prepared from:

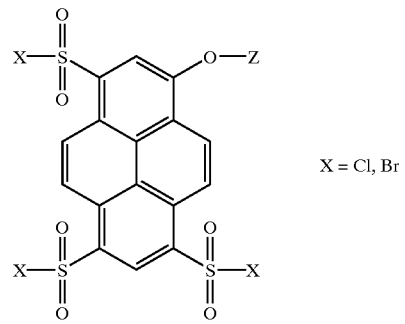

X = Cl, Br or from a dye monomer selected from the group consisting of:

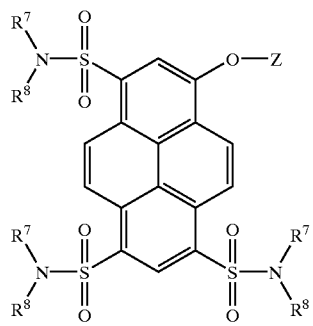

where $R^7$=—H, —CH$_2$—CH=CH$_2$ and when $R^7$=—H then $R^8$ is selected from —$R^9$—NH—(C=O)—(C=CH$_2$)—$R^{10}$, —$R^9$—O—(C=O)—(C=CH$_2$)—$R^{11}$, or —CH$_2$—C$_6$H$_4$—CH=CH$_2$, or where $R^9$ is lower alkylene having 2 to 6 carbon atoms, and where $R^{10}$ and $R^{11}$ are each —H, —CH$_3$ and when $R^7$ is —CH$_2$—CH=CH$_2$ then $R^8$ is —H, —CH$_2$—CH=CH$_2$, and Z is a blocking group that can be removed by hydrolysis selected from:

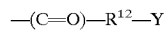
—(C=O)—$R^{12}$—Y where $R^{12}$ is a lower alkylene having 1 to 4 carbon atoms and Y is selected from —H, —OH, —CO$_2$H, —SO$_3$H, —(C=O)—NH—$R^{13}$, or —CO$_2$—$R^{13}$, where $R^{13}$ is a lower alkylene having 1 to 4 carbon atoms.

In another aspect of the method, the quencher $Q^1$ is selected from the group consisting of nitrogen containing conjugated heterocyclic aromatic bis-onium salts wherein the heterocyclic aromatic core is selected from the isomers of dipyridyl, phenanthroline, dipyridylethylene, dipyridylphenylene, and diazafluorene, and at least one of the substituents on the nitrogens is selected from ortho-, meta-, or para-benzyl boronic acids, preferably where both substituents are benzyl boronic acids wherein $Q^1$ is a discrete soluble molecule or is a pendant group or chain unit in a water soluble or dispersible or organic liquid soluble or dispersible polymer and said polymer optionally is non-covalently associated with an optional polymer matrix $M^1$ (as defined herein) when present and immobilized within said polymer matrix $M^1$.

In another aspect of the method, the quenchers $Q^1$ and $Q^2$ are derived from precursors selected from

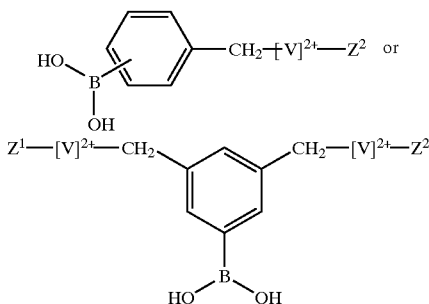

wherein $(V)^{2+}$ is a nitrogen containing conjugated heterocyclic aromatic group selected from isomers of dipyridyls, dipyridyl ethylenes, dipyridyl phenylenes, phenanthrolines, or diazafluorenes, wherein the two nitrogen atoms are each in a different aromatic ring and the nitrogens are in all positions capable of forming an onium salt; and $Z^1$ or $Z^2$ is either a polymerizable ethylenically unsaturated group selected from:

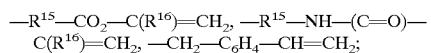

$R^{15}$ is a lower alkylene or hydroxyalkylene of 2 to 6 carbon atoms;

$R^{16}=$—H, —$CH_3$ or a coupling group selected from —$R^{17}$—$Z^3$, wherein $R^{17}$ is —$CH_2C_6H_4$— or alkylene of 2 to 6 carbon atoms, and $Z^3$ is selected from —OH, —SH, —$CO_2$H, or —$NH_2$.

For the dye D, note that $D^1$ and $D^2$ are defined with the proviso that the dye $D^1$ and $D^2$ do not include a diazo linkage —N=N—.

For the quencher Q, $Q^1$ and $Q^2$ are defined with the proviso that the quencher $Q^1$ and $Q^2$ do not include a diazo linkage —N=N—.

BRIEF DESCRIPTION OF THE FIGURES

FIG. 1A is the structural formula of N,N',N"-tris-(1-aminoethyl-2-polyethylene glycol (n~125)-methoxy-8-hydroxypyrene 1,3,6-tris-sulfonamide (HPTS-PEG).

FIG. 1B is the structural formula of N,N',N"-tris-(1-aminopropyl-3-methacrylamide)-8-acetoxy-pyrene-1,3,6-tris-sulfonamide (acetoxy-HPTS-MA)

FIGS. 2A to 2F are schematic representations of structures of quenchers $Q^1$ as the dihalide salts.

FIG. 2A is trans-1,2-bis(4,4'-N,N'-(benzyl-4-boronic acid)-pyridinium)ethylene dibromide;

FIG. 2B is 1,7-N;N'-bis(benzyl-3-boronic acid)-phenanthrolinium dibromide;

FIG. 2C is benzyl viologen (BV)-a comparative quencher;

FIG. 2D is 4,4'-N,N'-bis-(benzyl-2-boronic acid)-dipyridinium dibromide (o-BBV);

FIG. 2E is 4,4'-N,N'-bis-(benzyl-3-boronic acid)-dipyridinium dibromide (m-BBV);

FIG. 2F is 4,4'-N,N'-bis-(benzyl-4-boronic acid)-dipyridinium dibromide (p-BBV);

FIG. 3A is an unsymmetrical glucose responsive viologen, and FIGS. 3B to 3D are schematic representations of structures of quencher precursors:

FIG. 3A is 4-N-(benzyl-2-boronic acid)-4'-N-(benzyl)-dipyridinium bromide chloride;

FIG. 3B is 4-N-(benzyl-3-boronic acid)-4'-N,-(benzyl-4-ethenyl)-dipyridinium bromide chloride (m-SBBV);

FIG. 3C is 4-N-(benzyl-2-boronic acid)-4'-N'-(benzyl-4-ethenyl)-dipyridinium bromide chloride (o-SBBV); and FIG. 3D is 4-N-(benzyl-4-boronic acid)-4'-N'-(benzyl-4-ethenyl)-dipyridinium bromide chloride p-SBBV).

FIG. 3E is trans-1,2-bis-4-N-(benzyl-4-boronic acid)-4'-N'-(benzyl-4-ethenyl)-dipyridinium-4-ethylene dibromide;

FIG. 3F is 1-N-(benzyl-3-boronic acid)-4'-N'-(benzyl-3-ethenyl)-3 phenanthrolinium dibromide;

FIGS. 4A and 4B are schematic representations of the structures of the interpenetrating polymer network (IPN) polymers and semi-IPN polymers respectively of the invention.

FIG. 5 is a graphic representation of the response of benzyl viologen (0.001M) and 4,4'-N,N'-bis-(benzyl-3-boronic acid)-dipyridinium dibromide (m-BBV) showing modulation of m-BBV quenching efficiency toward HPTS-PEG ($1 \times 10^{-5}$ M) as a function of glucose concentration.

FIG. 6 is a graphic representation of the response of ortho-, meta-, and para-benzyl boronic acid viologen (BBV) (0.001M) showing modulation of quenching efficiencies to HPTS-PEG ($1 \times 10^{-5}$ M) as a function of glucose concentration.

FIG. 7 is a Stern-Volmer plot of m-BBV quenching of HPTS-PEG in pH 7.4 phosphate buffer.

FIG. 8 is a schematic representation of one embodiment of the in vitro probe as it would be used in a process stream.

FIG. 9 is a schematic representation of a second embodiment of the in vitro probe as it would be used in a process stream to monitor for polyhydroxyl organic compounds, e.g. glucose or fructose.

FIG. 10 is a schematic cross-sectional representation of the in vitro probe of FIG. 9.

DETAILED DESCRIPTION OF THE INVENTION AND PREFERRED EMBODIMENTS

Definitions

As used herein:

"Detector" refers to a device for monitoring light intensity such as a photo diode.

"Fluorophore" or "fluorophore dye" or "dye" refers to a compound that when exposed to light of appropriate wavelength emits light, i.e., it fluoresces.

"HEMA" refers to 2-hydroxyethylmethacrylate.

"Light source" or "excitation light source" refers to a device that emits electromagnetic radiation such as a xenon lamp, medium pressure mercury lamp, a light emitting diode (LED) all of which are commercially available.

"Linking group" refers to $L^1$ or $L^2$ which are divalent moieties, that covalently connect the sensing moiety to the polymer or matrix. Examples of $L^1$ or $L^2$ include those which are each independently selected from a direct bond or, a lower alkylene having 1 to 8 carbon atoms, optionally terminated with or including one or more divalent connecting groups selected from sulfonamide (—$SO_2NH$—), amide —(C=O)N—, ester —(C=O)—O—, ether —O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (as lower alkyl C1–C4 or benzyl) and the like.

"Onium" refers to a hetereoaromatic ionic compound having a formal positive charge on the heteroatom atom which in the case of the a viologen is nitrogen.

"Quencher" refers to a compound that reduces the emission of a fluorophore when in its presence.

"IPN" or "interpenetrating polymer network" refers to a combination of two or more network polymers synthesized in juxtaposition (see *Interpenetrating Polymer Networks*, L. H. Sperling, ed, ACS Advances in Chemistry Series 239, 1994, also from Aug. 25–30, 1991 New York ACS Meeting Abstracts).

"Semi-IPN" or semi-interpenetrating polymer network" refers to a combination of polymers in which one polymer is soluble and the other polymer is a network (see L. H. Sperling, above).

"PEG" or "polyethylene glycol" refers to polymer or chain segments which contain oxyethylene (—OCH$_2$—CH$_2$—) repeating units.

"PEGDMA" refers to polyethylene glycol terminated with two methacrylate groups.

"PEGMA" refers to polyethylene glycol terminated with one methacrylate group.

"Ultraviolet light range" refers to light in the spectrum between about 300 and 400 nm.

"Visible light range" refers to light in the spectrum between about 400 and 800 nm.

"Viologen" refers generally to compounds having the basic structure of a nitrogen containing conjugated N-substituted heterocyclic aromatic bis-onium salt, such as 4,4'-N,N'-bis-(benzyl) bipyridinium dihalide (i.e., dichloride), etc.

"Organic solvent" or "organic liquid" refers to solvents which dissolve the polyhydoxyl analytes of interest, typically these include polar water miscible solvents such as methanol, ethanol, tetrahydrofuran, dimethylformamide and the like.

The present invention concerns a number of important advances. These include but are not limited to an in vitro device for determining carbohydrate, 1,2-diol or 1,3-diol levels in liquids selected from aqueous or organic liquids or combinations thereof, a series of fluorophore dyes, a series of boronic acid substituted quenchers, and combinations of interacting water-compatible and water-soluble and organic solvent-compatible and organic solvent-soluble organic polymers. These aspects are discussed in more detail below. The components are discussed first, and their combination to produce the method and the device follows.

Quencher

The moiety that provides glucose recognition in the present invention is an aromatic boronic acid. More specifically, the boronic acid of this invention is covalently bonded to a conjugated nitrogen-containing heterocyclic aromatic bis-onium structure, e.g. a viologen, (see FIG. 2A and 2B) in which the boronic acid has a pKa less than 9 for in vitro applications, and reacts reversibly or irreversibly with glucose in aqueous, organic or combination media to form boronate esters. The extent of reaction is related to glucose concentration in the medium.

Bis-onium salts of this invention are prepared from conjugated heterocyclic aromatic dinitrogen compounds. The conjugated heterocyclic aromatic dinitrogen compounds are selected from dipyridyls, dipyridyl ethylenes, dipyridyl phenylenes, phenanthrolines, and diazafluorenes. It is understood that all isomers of said conjugated heterocyclic aromatic dinitrogen compounds in which both nitrogens can be substituted are useful in this invention. Bis-onium salts derived from 4,4'-dipyridyl are preferred.

One or more boronic acid groups are attached to the viologen molecule. Representative boronic acid groups include the following:

1. boronic acid substituted viologen of the structure:

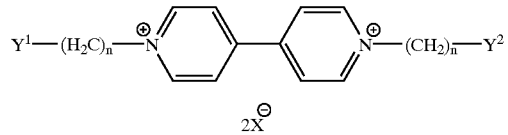

where n is 0–3, preferably n is 1, X is halogen (chloro or bromo), and where $Y^1$ and $Y^2$ include all isomers (o-, m-, and p-) of phenyl boronic acid or naphthyl boronic acid, preferably phenyl boronic acid more preferably m-phenyl boronic acid, and 2. as a substituent on the heterocyclic ring of a viologen.

The viologen is contemplated to include combinations of the above. Also, the viologen is also useful when unsymmetrically substituted, such as with a boronic acid functional group on one end and a polymerizable group, such as a vinyl group, on the other. The viologen/boronic acid moiety is a discrete soluble molecule or is a unit in the polymer backbone or is a pendant group on the polymer chain. Preferably, it is a pendant group or a unit in a water-soluble or dispersible-polymer, or a pendant group or a unit in a crosslinked, hydrophilic polymer or hydrogel sufficiently permeable to glucose to allow equilibrium to be established.

Fluorophore Dye

Representative dyes useful in this invention (See FIGS. 1A and 1B) are excited by light of wavelength about or greater than 300 nm, with a Stokes shift large enough that the excitation and emission wavelengths are separable, by at least 10 nm, and preferably greater than or equal to about 30 nm. These dyes are susceptible to quenching by electron acceptor molecules, such as viologens, are resistant to photo-bleaching, and are stable to photo-oxidation, hydrolysis, and biodegradation. Dyes useful in the present invention have an apparent Stern-Volmer quenching constant when tested with methyl viologen of about 50 or greater and preferably greater than 100. A general description of the Stern-Volmer test is found below in Procedure A. Preferred dyes include discrete and/or polymeric derivatives of hydroxypyrene trisulfonic acid. In some cases, the dye is bonded to a polymer through sulfonamide functional groups. The polymeric dyes are water-soluble, water-insoluble, organic solvent soluble or organic solvent insoluble but swellable or dispersible in water or solvent, or may be crosslinked. A preferred dye as a polymer is for example, a water-soluble PEG-dye adduct formed by reaction of acetoxypyrene trisulfonyl chloride with amino PEG monomethyl ether. The resulting dye polymer has a molecular weight of at least about 10,000 such that, when it is trapped in a hydrogel or network polymer matrix, it is incapable of diffusing out of the matrix into the surrounding medium. Other examples include soluble copolymers of N,N',N"-tris-(1-aminopropyl-3-methacrylamide)-8-acetoxy-pyrene-1,3,6-tris-sulfonamide with HEMA, PEGMA, or other hydrophilic comonomers. The phenolic substituent in the dye is protected during polymerization by a blocking group that is removed by hydrolysis after completion of polymerization. Such blocking groups which are suitable for example acetoxy, trifluoroacetoxy, and the like are well known in the art.

It is essential that, for sensing to occur, the sensing moieties (analyte, dye, quencher) must be in close physical proximity to allow interaction, i.e. mixed on a molecular level and in equilibrium with the species to be detected for quenching to occur. While not bound by theory, the groups may need to collide or the centers of the atoms need to be within about 10 angstroms for quenching to occur.

While not bound by any theory or mechanism, it appears that the intensity of the fluorescence emitted by the dye is attenuated by photo-induced intermolecular electron transfer from dye to viologen when viologen/boronic acid adduct and the dye are in close proximity. When glucose binds to the boronic acid, the boronate ester interacts with the viologen thereby altering its quenching efficacy according to the extent of glucose binding. The specific nature of this interaction is not yet established, but it may involve electron transfer from boronate to viologen or boronate formation may shift the reduction potential of the viologen. The reduction potential is an indicator of the ability of a quencher to accept an electron.

Polymer Matrix for Sensors

For normal in vitro use the sensing components are used as individual (discrete) components, the analyte, dye and quencher are mixed together in liquid solution, the change in fluorescence intensity is measured, and the components are discarded. Polymeric matrixes which are used to trap the components to prevent leaching are usually not present.

In other instances, the sensor is used in a static or moving stream of liquid which contains one or more polyhydroxyl organic compounds. Such streams include, for example, fermentation streams for wine, beer, pharmaceuticals and the like, food streams for carbonated beverages, fruit juice, dairy products and the like. Thus, for use in vitro in the stream, the sensing components are usually part of an organic polymer sensing assembly (see FIG. 8). Therefore, it is essential that none of the sensing moieties escape from the polymer assembly. Soluble dyes and quenchers can be confined by a semi-permeable membrane that allows passage of the analyte but blocks passage of the sensing moieties. This can be realized by using as sensing moieties soluble molecules that are substantially larger (molecular weight greater than about 1000, preferably greater than 5000) than the analyte molecules; and employing a dialysis or an ultrafiltration membrane with a specific molecular weight cutoff between the two so that the sensing moieties are quantitatively retained.

Preferably, the sensing moieties are immobilized by an insoluble polymer matrix which is freely permeable to glucose. The polymer matrix is comprised of organic, inorganic or combinations of polymers thereof The matrix may be composed of biocompatible materials. Alternatively, the matrix is coated with a second biocompatible polymer that is permeable to the analytes of interest. The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art.

Hydrogel polymers are preferred for this invention. The term, hydrogel, as used herein refers to a polymer that swells substantially, but does not dissolve in water. Such hydrogels may be linear, branched, or network polymers, or polyelectrolyte complexes, with the proviso that they contain no leachable fractions. Typically, hydrogel networks are prepared by a crosslinking step which is performed on water soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by a combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Such sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite which includes dispersions of a second polymer in a hydrogel matrix and alternating microlayer assemblies.

Monolithic hydrogels are typically formed by free radical copolymerization of a mixture of hydrophilic monomers, including but not limited to hydroxyethyl methacrylate (HEMA), PEGMA, methacrylic acid, hydroxyethyl acrylate, N-vinyl pyrrolidone, N,N' dimethyl acrylamide, and the like; ionic monomers include methacryloylaminopropyl trimethylammonium chloride, diallyl dimethyl ammonium chloride, vinyl benzyl trimethyl ammonium chloride, sodium sulfopropyl methacrylate, and the like; crosslinking agents include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is prepared from an ethylenically unsaturated derivative of a dye molecule, such as N,N',N"-tris-(1-aminopropyl-3-methacrylamide)-8-acetoxy-pyrene-1,3,6-tris-sulfonamide, the quencher moiety is prepared from an ethylenically unsaturated viologen such as 4-N-(benzyl-3-boronic acid)-4'-N'-(benzyl-4-ethenyl)-dipyridinium dihalide (m-SBBV). The concentration of dye is chosen to optimize emission intensity. The ratio of quencher to dye is adjusted to provide sufficient quenching to produce the desired measurable signal.

Alternatively, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2-hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

Polymers that are capable of reacting with boronic acids to form boronate esters under the conditions of this method are not useful as matrix polymers. Such polymers have 1,2- or 1,3-dihydroxy substituents, including but not limited to cellulosic polymers, polysaccharides, polyvinyl alcohol and its copolymers and the like.

Multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multi-component system is an interpenetrating polymer network (IPN) (see FIG. 4A) and most preferably a semi-interpenetrating polymer network (semi-IPN) (see FIG. 4B).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and polymerizing. Alternatively, a soluble quencher polymer is dissolved in a monomer mixture containing the dye monomer and the mixture polymerized. In either case, the molecular weight of the soluble component must be sufficiently high (about or greater than 10,000 daltons) that it cannot diffuse out of the network, i.e. it becomes physically bound to or trapped by the matrix.

In FIG. 4A, one group of polymer chains 41, 42, 43 and 44 contain the quencher, for example quencher $Q^2$. A second group of polymer chains 45, 46 and 47 containing the dye, for example, dye $D^2$, is formed at about the same time or sequentially. The points of crosslinking of the polymers are designated as 48 and 49. In FIG. 4B, one group of polymer chains 51, 52, 53 and 54 contain the quencher, for example, quencher $Q^2$. Dye $D^1$ is covalently bound to a second polymer 56. Crosslinking points 57 are designated.

The individual components in a multi-component hydrogel are made by the same or a different polymerization scheme. For example, in an IPN polymer, a first network is formed by free radical polymerization, the second by condensation polymerization. Likewise, in a semi-IPN polymer, the soluble component is formed by condensation polymerization and the network by free radical polymerization. For example, a quencher polymer, such as poly 4,4'-N,N'-bis(1,3-xylylene-5-boronic acid) bipyridinium dihalide is formed by condensing 4,4'-dipyridyl with 3,5-bis-bromomethyl phenylboronic acid. The quencher polymer is dissolved in a reaction mixture containing N,N',N"-trs-(1-aminopropyl-3-methacrylamide)-8-acetoxy-pyrene-1,3,6-tris-sulfonamide as is described above, and the solution is polymerized to obtain the semi-IPN hydrogel.

A Single Component Viologen Sensor

In another embodiment the invention is a boronic acid substituted viologen covalently bonded to a fluorophore. Preferably the adduct is a polymerizable compound or is a unit in a polymer. One such adduct for example is prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxy-pyrene-1,3,6-trisulfonyl chloride in a 1:1 mole ratio followed by reaction with excess PEG diamine to obtain a prepolymer mixture. An acid acceptor is included in both steps to scavange the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups are reacted with methacrylol chloride. After purification the dye/viologen monomer is copolymerized with HEMA and PEGDMA to obtain a hydrogel.

The advantage of this group of viologens is that dye and quencher are held in close proximity by covalent bonds which could lead to increased sensitivity. The disadvantage is that making these adducts is a formidable synthetic challenge and changes in composition are difficult to implement. Characterization and purification of the product is equally difficult. Therefore, the embodiments in which dye and quencher are separate entities are preferred.

Batch Optical Method of Analysis for Glucose

Measurements are carried out in a conventional luminescence spectrometer. A solution containing a dye and quencher of this invention buffered to pH=7.4 is prepared and loaded into a cuvet. The sample is excited by light of wavelength suitable for the dye being used and the fluorescence intensity measured. A fixed amount of the unknown glucose containing solution is added to the solution and the measurement is repeated. The change in intensity is used to calculate glucose concentration by reference to a calibration curve determined separately by measuring a standard series of glucose solutions and plotting the results as intensity change as a function of concentration. In this method, the sensing components need to be stable only for the time of the test, and the reaction with glucose need not be reversible.

Optical Method of Process Stream Analysis

A flow-through cell is fabricated for the luminescence spectrometer. A sensing polymer is mounted in the cell such that it is exposed on one surface to the excitation light and on the other to the process stream. A baseline is established by passing the process stream free of glucose through the cell and measuring the steady state fluorescence. The process stream is then passed through the cell and the fluorescence intensity monitored as a function of time. Glucose concentration is determined by reference to a calibration curve as described above. In this method, the sensor must be stable over time of operation and the reaction with glucose must be reversible. Further, the sensing moieties must be immobilized and not leach out into the process stream.

Device Configuration

FIG. 8 is a schematic representation of the device as used for one time or continuous monitoring for sugar, i.e. glucose.

The sensing polymer 81 which contains the dye and quencher may be attached to an optional support 82. For some embodiments an optional semi-permeable polymer membrane 83A is present. For other applications it may be useful to have an optional biocompatible coating 83B covering the entire assembly.

The light source 84 is connected to an optical filter 85 to an optical fiber 86 to the sensing polymer 81. Detector 87 is connected to an optical filter 88 to an optical fiber 89 which connects to sensing polymer 81. Light source 84 and detector 87 are both connected to electronic controller 90. Thus this system can detect changes in the sensing polymer caused by the sugar content of the analyte stream.

The device useful in vitro in a process stream and optionally for in vivo implanting and monitoring is shown in FIGS. 9 and 10. FIG. 9 shows the device for a process stream. FIG. 10 is the cross-sectional representation of the probe. For FIG. 9, light source 11 (visible and/or ultraviolet) is connected by optical fiber 12 to active cell 13. Semipermeable membrane 14 allows the analyte to enter and exit freely from cell 13. Optical fiber 15 conveys the altered light to filter 16, and optional photomultiplier to 17 to produce the analyte signal for analysis.

As shown in FIGS. 9 and 10, cell 13 includes the selectively permeable membrane such that the mixture of polymer 21, dye 22, and quencher 23 are retained in cell 13 under the conditions of analysis. The light enters cell 14 via optical fiber 12. Within the active portion of 14A of cell 14, the polymer 21, dye 22 and quencher 33 contact analyte 24 which selectively enter and exists in the cell causing a quantitative and reproducible change in the signal. This modified light signal travels optical fiber 15 to photomultiplier 17 to be analyzed.

The combination of components described herein produces a device for the determination of polyhydroxy substituted organic molecules in aqueous or organic solution. Typical aqueous solutions to be monitored for sugar level are found for example, in beer making, in wine making, in food and drink processing, in pharmaceutical compound manufacture, in antibiotic fermentation manufacture, in vaccine manufacture, and the like.

Experimental

Reagents and solvents are used as received from the commercial supplier unless otherwise noted. (See *Chem Sources USA* which is published annually.)

Halides include chloride, bromide or combinations thereof

The following examples are provided to be descriptive and exemplary only. They are not to be construed to be limiting in any manner or fashion.

Procedure A

Fluorescence Spectroscopy Analysis of the Apparent Stem-Volmer Quenching Constant of Methyl Viologen with a Fluorescent Dye The apparent Stern-Volmer quenching constant is derived from the slope of a Stern-Volmer plot of relative fluorescence intensity ($F_o/F$) versus concentration of quencher (M). See J. R. Lakowicz, (1999) *Principles of Fluorescence Spectroscopy Second Edition*, Kluwer Academic/Plenum Publishers, New York, pp. 237–289. One skilled in the art is in general able to perform this analysis for any fluorescent dye/quencher pair in a particular solvent of interest. This general Stern-Volmer analysis is used in determining the Stern-Volmer quenching constants in 0.1 ionic strength pH 7.4 phosphate buffer.

In order to avoid concentration quenching effects, the concentration of the dye is generally adjusted so that the optical density of the dye, at excitation $\lambda_{max} \leq 0.5$ absorption units. Once the desired dye concentration is determined, a stock dye solution is prepared in which the concentration is 5 times greater than that desired in the final measurements. For example, a dye for which the desired final concentration, which gives an optical density of excitation $\lambda_{max} \leq 0.5$ absorption units, is $1 \times 10^{-5}$ M, would require a stock solution in which the concentration is $5 \times 10^{-5}$ M.

Once determined, as is described above, 10 mL of dye stock solution of the appropriate concentration is made by weighing out the appropriate mass of dye and placing the solid into a 10 mL volumetric flask. The flask is then filled to the 10 mL mark with 0.1 ionic strength pH 7.4 phosphate buffer.

A stock solution of methyl viologen (25 mL, 0.0025 M) was prepared in a 10-mL volumetric flask with pH 7.4 phosphate buffer (0.1 ionic strength). Seven different solutions containing methyl viologen were then prepared in pH 7.4 phosphate buffer as described below in Table 1.

TABLE 1

| Volume dye standard (mL) | Volume quencher standard (mL) | Volume buffer (mL) | Final (dye) (M) | Final (Quencher) (M) |
| --- | --- | --- | --- | --- |
| 1 | 0.00 | 4.00 | 1.00E−05 | 0.00E+00 |
| 1 | 0.20 | 3.80 | 1.00E−05 | 1.00E−04 |
| 1 | 0.30 | 3.70 | 1.00E−05 | 1.50E−04 |
| 1 | 0.50 | 3.50 | 1.00E−05 | 2.50E−04 |
| 1 | 1.00 | 3.00 | 1.00E−05 | 5.00E−04 |
| 1 | 1.50 | 2.50 | 1.00E−05 | 7.50E−04 |
| 1 | 2.00 | 2.00 | 1.00E−05 | 1.00E−03 |

Each sample is then in-turn analyzed in a luminescence spectrometer set at the appropriate excitation wavelength and the appropriate emission wavelength range for the corresponding dye. The instrumental settings (slit widths, scan speed, optical filters, excitation wavelength, emission wavelength range) are held constant throughout the analysis of the series of samples). The emission fluorescence intensity is then determined as the integration of the fluorescence intensity over the emission wavelength range by the trapezoidal rule approximation method. The integrated values are plotted on the y-axis and the quencher concentrations are plotted on the x-axis and the slope of the resulting line is calculated by linear regression as the Stern-Volmer quenching constant. One skilled in the art will realize that based on quenching mechanism the Stern-Volmer plot may not result in a linear relationship. However through the use of the appropriate mathematical relationships, which is known and understood by one skilled in the art, the apparent Stern-Volmer quenching constant is calculated and used for comparison.

Preparation A

Synthesis of Dimethyl-(4-bromomethyl)-benzeneboronate

An oven-dried, 100-mL round bottom flask was cooled under argon, fit with a magnetic stir bar, and charged with (4-bromomethyl)-benzeneboronic acid (12.49 mmols, 2.684 g). The flask was sealed with a septum and charged with pentane (55 mL). The suspension was stirred at room temperature and upon addition of freshly distilled $CH_3OH$ (3.16 g, 4 mL, 97 mmols) the solution instantly clarified. After stirring for 20 minutes, the solution was dried over $MgSO_4$, then over $CaCl_2$ (to remove excess $CH_3OH$). The supernatant was cannulated, under argon, through a glass-fritted funnel (medium), and the pentane subsequently removed in vacuo. The remaining yellow oil was further dried under reduced pressure (0.1 torr, 1 hr). Yield: 1.6 g, 6.59 mmols (56%). $^1$H-NMR ($CD_3OD$, ppm): 4.5 (s, 2H), 7.4 (d, 2H), 7.55 (d, 2H). $^{11}$B-NMR ($CH_3OH$, ppm): 29 (s). Similar procedures were used to prepare the corresponding 2- and 3-isomers.

The products were used to make the boronic acid-viologen compounds of Examples 1–7.

Preparation B

Synthesis of 8-acetoxy-pyrene-1,3 6-trisulfonyl Chloride

Trisodium-8-acetoxy-pyrene-1,3,6-trisulfonate (acetoxy-HPTS, 11.33 g, 20 mmol) was suspended in 30 mL of thionyl chloride to which 5 drops of dimethylformamide was added. The suspension was refluxed for 3 hr., during which time it became a brown solution. The solution was then cooled to 25° C. under an argon atmosphere. Thionyl chloride was then distilled off under vacuum (2 Torr) leaving a yellow residue. The yellow residue was transferred to three separate centrifuge tubes along with 60 mL of dichloromethane. The suspensions were then centrifuged and the supernatant solutions transferred to a dry round bottom flask. The residue remaining in the centrifuge tubes was washed an additional four times each with 10 mL portions of dichloromethane. The supernatant solutions were combined and left overnight under an argon atmosphere and some precipitation was observed. The dichloromethane solution was added to 250 mL of pentane causing precipitation of a large amount of yellow solid. The supernatant was removed by a double ended needle and the yellow solid was dried on high vacuum (0.2 Torr). Yield: 8.62 g, 15.5 mmol (78%), $^1$H-NMR (500 MHz, $CDCl_3$, ppm): 2.682 (s, 3H), 8.833, (d, J=10 Hz, 1H), 8.915 (s, 1H), 9.458 (d, J=10 Hz, 1H), 9.509 (d, J=10 Hz, 1H), 9.630 (s, 1H), 9.685 (d, J=10 Hz, 1H). This product was used in Examples 8 and 10.

Preparation C

Synthesis of 4-(4-pyridyl)-N-(benzyl-4-ethenyl)-pyridinium Chloride

An oven-dried, 100-mL round bottom flask was cooled under argon, fit with a magnetic stir bar, and charged with 4,4'-dipyridyl (12.50 g, 80 mmols). The flask was sealed with a septum and charged with $CH_3OH$ (20 mL). The homogenous solution was stirred at room temperature while 4-(chloromethyl)styrene (2.82 mL, 20 mmols) was added dropwise via syringe. After stirring the solution at room temp for 48 hours, the solvent was removed in vacuo. Dry tetrahydrofuran (50 mL) was added to the reaction flask via cannula and the mixture stirred for three days, at which point the stirring was stopped, the solids allowed to settle, and the solvent was removed as much as possible via cannula. This process was repeated two more times, in each case reducing the mixing time to 24 hours. After the third trituration the mixture was filtered under nitrogen and washed with dry diethyl ether (200 mL) via cannula. The cake was dried by passing dry nitrogen through it under pressure for 1 hour, and finally by applying vacuum (0.1 torr, 1 h). Yield: 5.56 g, 18 mmols (90%), $^1$H-NMR ($D_2O$, ppm); 9.12 (d, 2H), 8.86, (d, 2H), 8.48 (d, 2H), 7.98 (d, 2H), 7.67 (d, 2H), 7.57 (d, 2H), 6.87 (dd, 1H), 5.92 (s, 2H), 5.45 (d, 1H). This compound was used in Examples 6 and 7.

EXAMPLE 1

Synthesis of 4,4'-N,N'-bis-(benzyl-3-boronic Acid)-Dipyridinium Dibromide

An oven-dried, 50-mL centrifuge tube was cooled under argon, fit with a magnetic stir bar, and charged with 4,4'-bipyridyl (0.469 g, 3 mmols). The tube was sealed with a septum and charged with $CH_3OH$ (7 mL). The homogenous solution was stirred at room temperature while freshly prepared dimethyl-(3-bromomethyl)-benzeneboronate (1.82 g, 7.5 mmols) was added via syringe. After stirring the solution for 15 hours, the reaction vessel was centrifuged (4 min at 3200 RPM) and the $CH_3OH$ cannulated to a separate flask. The remaining yellow solid was triturated with acetone:water (24:1, V/V, 25 mL), stirred vigorously on a vortex mixer and centrifuged. The acetone solution was removed by cannula and the trituration process repeated two more times. The solid was then triturated with diethyl ether using the same process. The pale yellow solid, in the centrifuge tube, was then dried on the high vacuum (0.6 torr, 2 hr). Yield: 0.956 g, 1.63 mmols (54%). MP: decomposition>230° C. $^1$H-NMR ($D_2O$, ppm): 6.093 (s, 4H), 7.715, (dd, 2H, $J_1$=7.5 Hz, $J_2$=7.5 Hz), 7.788 (d, 1H, J=7.5 Hz), 7.984 (s, 1H), 8.002 (d, 1H, J=7.5 Hz), 8.662 (d, 4H, J=7 Hz), 9.293 (d, 4H, J=7 Hz). $^{11}$B-NMR ($CH_3OH$, ppm): 29 (s).

This compound was used in Examples 17–19 below.

EXAMPLE 2

Synthesis of 4,4'-N,N'-bis-(benzyl-4-boronic Acid)-dipyridinium Dibromide

An oven-dried, 50-mL centrifuge tube was cooled under argon, fit with a magnetic stir bar, and charged with 4,4'-dypyridyl (0.234 g, 1.5 mmols). The tube was sealed with a septum and charged with anhydrous $CH_3OH$ (7 mL). The homogenous solution was stirred at room temperature while freshly prepared dimethyl-(4-bromomethyl)-benzeneboronate (1.09 g, 4.5 mmols) was added via syringe. After stirring the solution for 15 hours, the reaction vessel was centrifuged (4 min at 3200 RPM) and the $CH_3OH$ cannulated to a separate flask. The remaining yellow solid was triturated with acetone:water (24:1, V/V, 25 mL), stirred vigorously on a vortex mixer, and centrifuged. The acetone solution was removed by cannula and the trituration process repeated two more times. The solid was then triturated with diethyl ether using the same process. The pale yellow solid, in the centrifuge tube, was then dried under reduced pressure (0.6 torr, 2 hr). Yield: 0.723 g, 1.63 mmols (82%). MP: decomposition greater than 230° C. $^1$H-NMR ($D_2O$, ppm): 6.116 (s, 4H), 7.670 (d, 4H, J=8.25 Hz), 8.017 (d, 4H, J=8.25 Hz), 8.698 (d, 4H, J=6.5 Hz), 9.325 (d, 4H, J=6.5 Hz). $^{11}$B-NMR ($CH_3OH$, ppm): 29 (s).

This compound was found to quench the fluorescence of the dye of Example 9 and to respond to glucose.

EXAMPLE 3

Synthesis of 4,4'-N,N'-bis-(benzyl-2-boronic Acid)-dipyridinium Dibromide

An oven-dried, 50-mL centrifuge tube is cooled under argon and fit with a magnetic stir bar. 4,4'-Bipyridyl (1.5 mmol, 0.234 g) is weighed out into the tube which is then sealed with a septum and charged with $CH_3OH$ (7 mL). The homogenous solution is stirred at room temperature while mixing. Freshly prepared dimethyl-(2-bromomethyl)-benzeneboronate (4.5 mmols, 1.2 mL, 1.09 g) is added via syringe to the reaction tube and the resulting brown/orange solution is stirred at room temperature (ambient) for 15 hrs. The reaction vessel is then centrifuged (4 min at 3200 RPM) and the $CH_3OH$ cannulated to a separate flask. The remaining yellow solid is triturated with diethyl ether (25 mL), stirred vigorously using a vortex mixer, and centrifuged. The ether solution is removed by cannula and the trituration process repeated three more times. The pale yellow solid, in the centrifuge tube, is then dried under reduced pressure (0.6 torr, 2 hr). The yield is 70%. $^1$H-NMR (D2O, ppm): 6.21 (s, 2H), 7.72, (m, 3H), 7.91 (d, 1H), 8.60 (d, 2H), 9.18 (d, 2H). $^{11}$B-NMR ($CH_3OH$, ppm) 30.2 (broad s).

This compound was found to quench the fluorescence of the dye of Example 9 and to respond to glucose.

EXAMPLE 4

Synthesis of Trans-1,2-bis(4,4'-N,N'-(benzyl-4-boronic Acid)-pyridinium)Ethylene Dibromide An oven-dried, 50-mL centrifuge tube was cooled under argon, fit with a magnetic stir bar, and charged with trans-1,2-Bis(pyridyl)ethylene (0.518 g, 2.8 mmols). The tube was sealed with a septum, charged with anhydrous $CH_3OH$ (7 mL), and freshly prepared dimethyl-(4-bromomethyl)-benzeneboronate (7.1 mmols, 1.725 g) was added via syringe. The homogenous solution was stirred at room temperature for 49 hrs. The $CH_3OH$ was removed in vacuo and the remaining solid was triturated with diethylether (2×40 mL). The suspension was filtered through a glass-fritted funnel (medium), and the solid was dried under reduced pressure (0.1 torr) for 30 minutes. At this point the $^1$H-NMR still showed the presence of impurities. Thus, the solid was placed in acetone:water (70 mL, 24:1, V/V) and allowed to sit overnight. The slurry was filtered and then dried under reduced pressure (0.1 torr) for one hour. It was subsequently isolated under argon. Yield: 1.482 g, 2.42 mmols (86%). MP: >230° C. $^1$H-NMR ($D_2O$, ppm): 5.992 (s, 4H), 7.652 (d, 4H, J=7.5 Hz), 7.855 (d, 4H, J=7.5 Hz), 8.234 (s, 2H), 8.534 (d, 4H, J=6.5 Hz), 9.221 (d, 4H, J=6.5 Hz) $^{11}$B-NMR ($CD_3OD$, ppm): 29 (s).

This compound was found to quench the fluorescence of the dye of Example 9 and to respond to glucose.

EXAMPLE 5

Synthesis of 1,7-N,N'-bis(benzyl-3-boronic Acid)-phenanthrolinium Dibromide

An oven-dried, 50-mL centrifuge tube was cooled under argon, fit with a magnetic stir bar, and charged with 1,7-phenanthroline (0.288 g, 1.6 mmols). The tube was then sealed with a septum, charged with $CH_3OH$ (4 mL), and freshly prepared dimethyl-(3-bromomethyl)-benzeneboronate (0.972 g, 4 mmols) was added via syringe. The homogenous solution was stirred at room temperature for 15 hrs, and then refluxed for 2 hrs. The reaction mixture was cooled to room temperature under argon and the $CH_3OH$ was removed in vacuo. The yellow/orange solid was triturated overnight with acetone:water (40 mL. 24:1, V/V), then with diethyl ether (2×40 mL). The suspension was filtered through a glass-fritted funnel (medium), and the solid isolated under argon. Yield: 0.495 g, 0.812 mmols (51%). MP: >230° C. $^1$H-NMR ($D_2O$, ppm): 6.504 (1H), 7.638 (1H), 8.025 (m, 2H), 8.2505 (d, 1H, 8.5 Hz), 8.483 (m, 6H) 8.738 (d, 1H, J=8.5 Hz), 9.315 (d, 1H, J=5.75 Hz), 9.605 (d, 1H, J=5.75 Hz), 10.098 (d, 1H, J=8.5 Hz) 10.269 (d, 1H, J=8.5 Hz). $^{11}$B-NMR ($CH_3OH$, ppm): 28 (s).

This compound was found to quench the fluorescence of the dye of Example 9 and respond to glucose.

EXAMPLE 6

Synthesis of 4-N-(benzyl-4-boronic Acid)-4'-N'-(benzyl-4-ethenyl)-dipyridinium Bromide Chloride An oven-dried, 50-mL centrifuge tube was cooled under argon, fit with a magnetic stir bar, and charged with 4-(4-pyridyl)-N-(benzyl-4-ethenyl)-pyridinium chloride (0.463 g, 1.5 mmols). The tube was sealed with a septum and charged with acetonitrile (6 mL). The resulting pink/orange suspension was stirred at room temperature while freshly prepared dimethyl-(4-bromomethyl)-benzeneboronate (0.486 g, 2 mmols) was added via syringe. After stirring the suspension for 23 hrs the reaction vessel was centrifuged (4 min at 3200 RPM) and the acetonitrile cannulated to a separate flask. The remaining yellow solid was triturated with acetone:water (25 mL, 24:1, V/V), stirred vigorously on a vortex mixer, and centrifuged. The acetone solution was removed by cannula and the trituration process repeated two more times. The solid was then triturated with diethyl ether using the same process. The bright yellow solid, in the centrifuge tube, was then dried under reduced pressure (0.5 torr, 1 hr). Yield: 0.431 g, 0.824 mmols (55%). MP: >200° C. $^1$H-NMR ($D_2O$ ppm): 5.405 (d, 1H, J=11.5 Hz), 5.929 (d, 2H, J=17.5 Hz), 5.934 (s, 2H), 5.981 (s, 2H), 6.832 (dd, 2H, $J_1$=17.5 Hz, $J_2$=11 Hz), 7.523 (d, 2H, J=9 Hz), 7.562 (d, 2H, J=8 Hz), 7.626 (d, 2H, J=8 Hz), 7.8815 (d, 2H J=8.5 Hz), 8.566 (dd, 4H, $J_1$=3.6 Hz, $J_2$=1.5 Hz), 9.1855 (dd, 4H, $J_1$=6.5 Hz, $J_2$=6 Hz). $^{11}$B-NMR ($CH_3OH$, ppm): 28 (s).

This compound was found to quench the fluorescence of the dye of Example 9 and to respond to glucose.

EXAMPLE 7

Synthesis of 4-N-(benzyl-3-boronic Acid)-4'-N'-(benzyl-4-ethenyl)-dipyridinium Bromide Chloride An oven-dried, 50-mL centrifuge tube was cooled under argon, fit with a magnetic stir bar, and charged with 4-(4-pyridyl)-N-(benzyl-4-ethenyl)-pyridinium chloride (0.463 g, 1.5 mmols). The tube was sealed with a septum and charged with acetonitrile (6 mL). The resulting pink/orange suspension was stirred at room temperature while freshly prepared dimethyl-(3-bromomethyl)-benzeneboronate (0.486 g, 2 mmols) was added via syringe. After stirring the suspension for 23 hours the reaction vessel was centrifuged (4 min at 3200 RPM) and the acetonitrile cannulated to a separate flask. The remaining yellow solid was triturated with acetone:water (25 mL, 24:1, V/V), stirred vigorously on a vortex mixer, and allowed to sit overnight. The acetone solution was removed by cannula and the solid then triturated with diethyl ether (3×25 mL); each time the triturant was removed via cannula. The remaining bright yellow solid, in the centrifuge tube, was then dried under reduced pressure (0.015 torr, 3 hr). Yield: 0.584 g, 1.12 mmols (74%). MP: decomposition greater than 150° C. $^1$H-NMR ($D_2O$, ppm): 5.5165 (d, 1H, J=10.75 Hz), 6.0435 ppm (d, 1H, J=17.8 Hz), 6.095 (s, 2H), 6.049 (s, 2H), 6.9433 (dd, 1H, $J_1$=11.5 Hz, $J_2$=17.9 Hz), 7.626 (m, 4H), 7.724 (m, 2H), 7.979 (s, 1H), 7.994 (d, 1H, J=7.5 Hz), 8.648 (d, 4H), 9.280 (d, 4H). $^{11}$B-NMR ($CH_3OH$, ppm): 28 (s).

This compound was used to make the polymers of Examples 11, 12, 15, and 16.

EXAMPLE 8

Synthesis of N,N',N"-tris-(1-aminoethyl-2-polyethylene glycol(n~125)methoxy)-8-acetoxy-pyrene-1,3,6-tris-sulfonamide A 250-mL round bottom flask was equipped with a magnetic stir bar and charged with 170 mL of dry tetrahydrofuran (THF). Methoxy-polyethyleneglycol (PEG)-amine (5.65 g, 5630 g/mol, 1 mmol) was added to the flask along with 0.5 grams of granular $CaH_2$. The mixture was heated to 30° C. for 24 hr with stirring. Diisopropylethylamine (0.6 mL, 129.24 MW, 0.742 g/mL, 3.4 mmol) was added to the flask and the mixture allowed to stir for an additional hr. The flask was cooled to room temperature and filtered through an air sensitive glass fritted filtration apparatus to remove excess $CaH_2$ and $Ca(OH)_2$. The THF solution was placed back into a 250 mL round bottom flask with magnetic stir bar and heated to 30° C. with stirring. 8-Acetoxy-pyrene-1,3,6-trisulfonyl chloride (0.185 g, 624.8 g/mol, 0.3 mmol) was added to the warm THF solution. The solution immediately turned a deep blue color and faded to a red wine color over 15 min. The reaction was stirred at 30° C. for 24 hr. The solvent was removed by rotary evaporation and the residue was dissolved in 100 mL of 1 M HCl. The aqueous solution was extracted with methylene chloride (3×100 mL). The methylene chloride fractions were combined and the solvent was removed by reduced pressure evaporation to yield compound as a red solid. Yield: about 5.5 g (~97%). FTIR (KBr pellet, $cm^{-1}$): 842, 963, 1060, 1114, 1150, 1242, 1280, 1343, 1360, 1468, 1732, 2525, 2665, 2891. 1. This product was then used in Examples 9 and 12.

EXAMPLE 9

Synthesis of N,N',N"-tris-(1-aminoethyl-2-polyethylene Glycol(n~125))-8-hydroxy-pyrene-1,3,6-tris-sulfonamide Approximately 5.5 g of N,N',N"-tris-1-aminoethyl-2-polyethylene glycol (n~125)methoxy-8-acetoxy-pyrene-1,3,6-tris-sulfonamide was dissolved in 100 mL of 1 M NaOH and stirred for 2 hr. The aqueous solution was neutralized to pH 7 and extracted with methylene chloride (3×100 mL). The methylene chloride fractions were combined and reduced to approximately 10 mL by rotary evaporation. The concentrated methylene chloride solution was then added dropwise into 400 mL of vigorously stirred diethyl ether in an Erlenmeyer flask. The diethyl ether was filtered using a Buchner funnel. The product was isolated as an orange powder. Yield: 5.425 g, 0.31 mmol (94%). FTIR (KBr pellet, $cm^{-1}$): 842, 963, 1060, 1110, 1150, 1242, 1281, 1343, 1360, 1468, 2888. This compound was identified as the trisubstituted sulfonamide derivative by Fourier Transform Infrared (FTIR). The sulfonic acid IR stretch occurs at 1195.7 $cm^{-1}$. There is no 1195.7 $cm^{-1}$ stretch in the FTIR of this compound. Instead a stretch of 1110 $cm^{-1}$, assigned to the sulfonamide, is observed. When dissolved in pH 7.4 buffer, the fluorescence of this compound is quenched by methyl viologen with an apparent Stem-Volmer quenching constant of 319$M^{-1}$.

This was quenched by the products of Examples 1–7 and used in Examples 17–20.

EXAMPLE 10

Synthesis of N,N',N"-tris-(1-aminopropyl-3-methacrylamide)-8-acetoxy-pyrene-1,3,6-tris-sulfonamide (Acetoxy-HPTS-MA)

A 100-mL round bottom flask was charged with aminopropyl-3-methacrylamide HCl salt (2.68 g, 15 mmol) and 50-mL of acetonitrile to give a white suspension. Water was added dropwise while stirring until all of the white suspension had disappeared producing two layers. Potassium carbonate was added and the suspension was stirred for 15 minutes. The supernatant was transferred to a 500-mL round bottom flask and the potassium carbonate was washed with 50-mL acetonitrile which was then combined in the 500-mL round bottom flask. A yellow solution of acetoxy-HPTS-Cl (1.03 g, 1.8 mmol), 200-mL acetonitrile, and 20-mL dichloromethane was added under argon to the 500-mL round bottom flask containing the free amine in acetonitrile causing the solution to turn dark red with precipitate formation. The solution was stirred for 1 hr and the supernatent was transferred and concentrated under vacuum to give a dark residue. The residue was extracted with water (1000 mL) and a 50:50 acetonitrile/ethyl acetate solution (700 mL). The organic extract was washed with an additional 1000 mL water. The organic extract was dried over magnesium sulfate and concentrated on a rotary evaporator to give a red residue which was dissolved in methanol. The methanol solution was concentrated and the resulting red residue was dried under high vacuum to give a red solid which was the unprotected HPTS-MA. Yield: 420 mg, 0.5 mmol, 28%. $^1$H-NMR (500 MHz, $D_4$-methanol, ppm): 1.617 (p, J=6.5 Hz, 8H), 1.781 (s, 3H), 1.767 (s, 6H), 2.934 (p, J=6.5 Hz, 9H), 3.158 (mult. 8H), 5.211 (t, J=1.5 Hz), 5.229 (t, J=1.5 Hz), 5.488 (s, 1H), 5.510 (s, 2H), 8.290 (s, 1H), 8.837 (d, J=9.5 Hz, 1H), 8.913 (d, J=9.5 Hz, 1H), 8.988 (d, J=1.5 Hz 1H), 9.201 (d, J=9.5 Hz, 4H), 9.222 (s, 1H). Unprotected HPTS-MA (100 mg, 0.1 mmol) was then suspended in 10 mL acetic anhydride and a catalytic amount of sodium acetate was added and the suspension refluxed for 2 hr. Acetic anhydride and acetic acid were removed under vacuum and the resulting brown residue was extracted with 20 mL acetonitrile. The extract was dripped into 150 ml diethyl ether causing the precipitation of a brown solid. Yield: 75 mg, 0.09 mmol (86%).

This monomer was used in Examples 14–16.

EXAMPLE 11

Copolymerization of 4-N-(benzyl-3-boronic Acid)-4'-N'-(benzyl-4-ethenyl)-dipyridinium Bromide Chloride into a Water-soluble Polymer A 50-mL cone-shaped round bottom flask was charged with 2-hydroxyethyl methacrylate (1.50 g, 11.5 mmols), 4-N-(benzyl-3-boronic acid)-4'-N'-(benzyl-4-ethenyl)-dipyridinium bromide chloride (0.1 g, 0.191 mmols), and 3-((methacryloylamino)propyl)) trimethyl ammonium chloride (0.50 g, 2.27 mmols). After the flask was sealed with a septum, the solution was vigorously stirred on a vortex mixer. The vessel was then charged with isopropyl alcohol:water (8 mL, 1:1, V/V) and deoxygenated with argon for one hr. Concurrently, in a separate 100-mL, side-armed round bottom flask, a solution of 2,2'-azobisisobutyronitrile (AIBN, 100 mg, 0.609 mmols) in isopropyl alcohol:water (5 mL) was prepared. The flask was equipped with a magnetic stir bar and a condenser, and deoxygenated with argon for one hour. The entire monomeric solution was taken-up by syringe and 1 mL was added, through the sidearm, to the AIBN solution. The AIBN reaction vessel was then placed in a 70° C. oil bath and the remaining monomeric mixture added via syringe pump over 6 hrs (1.5 mL/hr). The resulting orange solution was cooled to room temperature under argon and the solvent carefully removed in vacuo. The amorphous solid was dissolved in $CH_3OH$ (20 mL) and quantitatively transferred to a centrifuge tube via cannula.

After addition of diethyl ether (20 mL) and formation of a white precipitate, the product was isolated via centrifugation (4 min @ 3200 RPM). It was washed with diethyl ether (30 mL), dried under reduced pressure (0.5 torr, 3 hrs), and isolated under an inert atmosphere of argon. Yield: 1.345 g, (67 Wt %). The amount of viologen moiety incorporated into the polymer was determined, by UV absorbance, to be greater than 99% of the expected value.

This product was used in Example 20.

EXAMPLE 12

Semi-IPN: the Thin Film Copolymerization of 4-N-(benzyl-3-boronic Acid)-4'-N-(benzyl-4-ethenyl)-dipyridinium Bromide Chloride Using HPTS-PEG A 10-mL volumetric flask was charged with 2-hydroxyethyl methacrylate (3.525 g, 27.08 mmols), 4-N-(benzyl-3-boronic acid)-4'-N'-(benzyl-4-ethenyl)-dipyridinium bromide chloride (0.039 g, 0.075 mmols), 3-[(methacryloylamino)propyl] trimethyl ammonium chloride (0.3 g, 1.36 mmols), polyethylene glycol dimethacrylate (1.11 g, 1.11 mmols), 2,2'-azobis [2-(2-imidazolin-2-yl)propane]dihydrochloride (0.025 g, 0.077 mmols), and N,N',N"-tris-(1-aminoethyl-2-polyethyleneglycol(n~125)-methoxy-8-hydroxy-pyrene 1,3,6-tris-sulfonamide (0.013 g, $7.5 \times 10^{-4}$ mmols); it was filled to the 10-mL mark with isopropyl alcohol:water (1:1, V/V). After the solution was vigorously stirred on the vortex mixer it was transferred, via pipette, to a 50-mL, cone-shaped round bottom flask and deoxygenated with argon for one hour. The monomer solution was taken-up by syringe and the syringe attached to the polymerization chamber. The solution was then inserted into the cell, under argon, to fill the entire cavity of the cell. The chamber was sealed with Teflon plugs and wrapped in two ZIPLOC® freezer bags. The entire unit was submerged in a 40° C. water-bath and heated for 17 hrs. The polymerization chamber was removed from the bath and the bags, and subsequently disassembled to afford a thin green polymeric film. The polymeric film was leached and stored under pH 7.4 phosphate-buffer. This product was used in Example 13.

The polymerization chamber was comprised of (1) An IR cell-holder: two stainless steel plates fashioned to contain the cell and the luer ports; (2) A Cell: two glass plates containing a TEFLON® 0.02" spacer in between, with holes drilled through the top plate and spacer; and (3) A Gasket: a precision-cut rubber spacer used to the seal the cell to the cell-holder.

EXAMPLE 13

Fluorescence Spectroscopy Analysis of Semi-IPN: Copolymer of 4-N-(benzyl-3-boronic Acid)-4'-N'-(benzyl-4-ethenyl)-dipyridinium Bromide Chloride (m-SBBV) Using HPTS-PEG A 10-mm path length, 5-mL disposable polystyrene cuvet was modified using a hot metal rod to melt a 3.9 mm diameter hole into the bottom center of the cuvet. While the plastic was still malleable the threads of a 10–32 standard thread, ⅛" I.D. hose end adapter were screwed into the plastic. The plastic was allowed to cool and the adapter was unscrewed. TEFLON® thread tape was applied to the threads. The adapter was then refit into the cuvet. A disposable polyethylene cuvet cap was modified similarly by puncturing a hole in the center of the cap and threading into the hole an identical 10–32 standard thread to ⅛" I.D. hose adapter. A thin sheet of clear plastic was then cut into a 35×9 mm rectangle and a window 6×15 mm was cut out of the center. Two pressure fittings were constructed from the plunger of a Tuberculin Monoject 1-mL syringe. They were used to put pressure on the plastic mask to hold the polymer in place within the cuvet. The round thumb button of the plunger was used as the pressure plate and was removed from the shaft such that the height of the bottom of the plate to the top of the shaft was 9 mm. The flow-through-cell was then assembled such that the polymer film was in the center of the cuvet and the clear plastic mask directly over it, effectively framing the film with its window. The pressure fittings were then put in place using tweezers, one at the bottom of the cell and one at the top, oriented with the broad base against the plastic mask. The outside wall of the cuvet cap, which sits inside the cuvet, was then coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face first in the front surface adapter). ⅛" TYGON® PTFE tubing was connected to the hose adapters of the flow-through-cell. The orientation of the front surface adapter was optimized so that the emission detector was sensing only the surface of the polymer. A peristaltic pump was used to circulate pH 7.4 phosphate buffer (ionic strength 0.1) through the cell at a rate of 30 mL per minute. The time drive function of the Perkin-Elmer LS50B software was used to acquire fluorescence intensity readings every ten sec with an integration time of two seconds. The excitation frequency was set at 475 nm and the emission frequency was set at 536 nm. The excitation and emission slit widths were set at 2.5 nm. A base line value of 358 (fluorescence intensity) was established with buffer solution. The peristaltic pump was stopped and the pumping solution was changed to 1800 mg/dl glucose in pH 7.4 phosphate buffer. The fluorescence intensity increased 127 units to a value of 485, corresponding to a 35% signal increase (S/N ratio=72). After switching back to buffer the signal approached the expected baseline value of 358.

EXAMPLE 14

N,N',N"-tris-(1-aminopropyl-3-methacrylamide)-8-hydroxypyrene-1,3,6-tris-sulfonamide Hydrogel Polymer A 16-mm NMR tube modified with a female 14/20 ground glass joint was charged with a mixture of isopropyl alcohol/water (1:1, 1.5 mL), HEMA (750 mg), polyethylene glycoldimethacrylate (PEGDMA, n~25) (200 mg), 3-(methacryloylamino)propyltrimethyl ammonium chloride (TMAC) (50 mg), N,N',N"-tris-(1-aminopropyl-3-methacrylamide)-8-acetoxypyrene-1,3,6-tris-sulfonamide (acetoxy-HPTS-MA) (1 mg, $1.2 \times 10^{-6}$ mols), and (2,2'-azobis-2(2-imidazolin-2-yl)propane) hydrochloride (VA-044 free radical initiator) (5 mg). All solids were dissolved with the aid of a vortex mixer. The NMR tube was then fitted with a male 14/20 ground glass joint TEFLON® stop cock to vacuum adapter. The mixture was then de-oxygenated via 4 freeze/pump/thaw cycles (−78° C., 1 torr, 5 min. and thawed under nitrogen. The NMR tube was then heated in a water bath at 40° C. (±0.5° C.) for 12 hr. The glass NMR tube was carefully broken to free the polymer plug. The polymer was dialyzed in 200 mL of de-ionized water with triethylamine (5 drops) (de-ionized water and amine solution was changed every 24 hr for 7 days) to remove the acetoxy protecting group on the acetoxy-HPTS-MA. The resulting polymer plug was cut into about 5-mm slices and analyzed by fluorescence spectroscopy.

Excitation and emission spectra of the gels are substantially identical to spectra obtained for the PEG adduct (Example 4). Samples of the polymer gel suspended in pH 7.4 buffer are visibly fluorescent when examined in daylight. The fluorescence is noticeably diminished when m-SBBV, o-SBBV, or p-SBBV was added to the aqueous phase. The fluorescence was recovered when glucose is added to the solution. Similar gels were prepared with dye concentrations of 0.05 to 5 mg/g polymer (dry weight). All were yellow-green to orange in color and were visibly fluorescent when examined in day (natural) light.

The fluorescence was quenched when the hydrogels were exposed to aqueous o-, m-, and p-BBV.

EXAMPLE 15

IPN: Copolymerization of 4-N-(benzyl-3-boronic Acid)-4'-N'-(benzyl-4-ethenyl)-dipyridinium Bromide Chloride (M-SBBV) Using HPTS-MA Monomeric quencher solution: A 10-mL volumetric flask was charged with 2-hydroxy ethyl methacrylate (27.08 mmols, 3.525 g), 4-N-(benzyl-3-boronic acid)-4'-N'-(benzyl-4-ethenyl)-dipyridinium bromide chloride (0.197 mmols, 0.103 g), 3-((methacryloylamino)propyl) trimethyl ammonium chloride (1.36 mmols, 0.30 g), polyethylene glycol dimethacrylate (1.11 mmols, 1.11 g), and 2,2'-azobis (2-(2-imidazolin-2-yl)propane)dihydrochloride (0.077 mmols, 0.025 g); it was filled to the 10-mL mark with isopropyl alcohol:water (1:1, V/V). The solution was vigorously stirred on the vortex mixer until homogenous.

Polymeric Dye Powder: A 10-mL volumetric flask was charged with 2-hydroxy ethyl methacrylate (27.08 mmols, 3.525 g), 3-((methacryloylamino)propyl) trimethyl ammonium chloride (1.36 mmols, 0.3 g), polyethylene glycol dimethacrylate (1.11 mmols, 1.11 g), 2,2'-azobis (2-(2-imidazolin-2-yl)propane)dihydrochloride (0.077 mmols, 0.025 g), and N,N',N"-tris-(1-aminopropyl-3-methacrylamide)-8-acetoxy-1,3,6-tris-sulfonamide (7.5×$10^{-4}$ mmols, 6.6×$10^{-4}$ g); it was filled to the 10-mL mark with isopropyl alcohol:water (1:1, V/V). After the solution was vigorously stirred on the vortex mixer it was transferred, via pipette, to a 50-mL round-bottom flask and the flask was sealed with a rubber septum; it was deoxygenated with argon for 30 minutes. The monomeric solution was taken-up by syringe and the needle was capped with a rubber stopper. It was then transferred to an argon-filled glove box along with the polymerization chamber*. The syringe was attached to the polymerization chamber and the solution was inserted into the cell, under argon, to fill the entire cavity. The chamber was sealed with TEFLON® plugs and wrapped in a ZIPLOC® freezer bag. The entire unit was transferred to an oven and heated to 40° C. for 14 hrs. The polymerization chamber was removed from the oven and the bags, and subsequently disassembled to afford a thin green polymeric film. The film was leached with 500 mL of distilled water (pH 5) for six hours; fresh water was replaced every two hours. The thin film was then dried under reduced pressure (40° C., 20 in Hg, 3 hours), brought to –196° C. and crushed into a fine powder using a mortar and pestle.

* The polymerization chamber was comprised of (1) An IR cell-holder: two stainless steel plates fashioned to contain the cell and the luer ports; (2) A Cell: two glass plates containing a Teflon 0.02" spacer in between, with holes drilled through the top plate and spacer; and (3) A Gasket: a precision-cut rubber spacer used to the seal the cell to the cell-holder.

Interpenetrating network copolymer: A 50-mL round-bottom flask was charged with monomeric quencher-solution (5.2 mL) and polymeric dye-powder (0.169 g). The mixture was vigorously stirred on the vortex mixer for 10 minutes to allow the liquid to be imbibed by the dye particles and then deoxygenated with argon for 15 minutes. The heterogeneous solution was taken-up by syringe and the needle was capped with a rubber stopper. It was then transferred to an argon-filled glove box along with the polymerization chamber*. The syringe was attached to the polymerization chamber and the solution was inserted into the cell, under argon, to fill the entire cavity. The chamber was sealed with TEFLON® plugs and wrapped in a ZIPLOC® freezer bag. The entire unit was transferred to an oven and heated to 40° C. for 14 hrs. The polymerization chamber was removed from the oven and the bag, and subsequently disassembled to afford a thin, orange, gel-integrated polymeric film. The film was placed in a pH 8-NaOH solution for 12 hours, then leached and stored in pH 7.4 phosphate-buffer.

* The polymerization chamber was comprised of (1) An IR cell-holder: two stainless steel plates fashioned to contain the cell and the luer ports; (2) A Cell: two glass plates containing a Teflon® 0.02" spacer in between, with holes drilled through the top plate and spacer; and (3) A Gasket: a precision-cut rubber spacer used to the seal the cell to the cell-holder.

This product was used in Example 21.

EXAMPLE 16

Two Component System: The Thin Film Copolymerization of 4-N-(benzyl-3-boronic Acid)-4'-N'-(benzyl-4-ethenyl)-dipyridinium Bromide Chloride (M-SBBV) Using HPTS-MA A 10-mL volumetric flask was charged with 2-hydroxyethyl methacrylate (3.525 g, 27.08 mmols), 4-N-(benzyl-3-boronic acid)-4'-N'-(benzyl-4-ethenyl)-dipyridinium bromide chloride (0.039 g, 0.075 mmols), 3-((methacryloylamino)propyl) trimethyl ammonium chloride (0.3 g, 1.36 mmols), polyethylene glycol dimethacrylate (1.11 g, 1.11 mmols), 2,2'-azobis (2-(2-imidazolin-2-yl)propane)dihydrochloride (0.025 g, 0.077 mmols) and N,N',N"-tris-(1-aminopropyl-3-methacrylamide)-8-acetoxy-1,3,6-tris-sulfonamide (6.6×$10^{-4}$ g, 7.5×$10^{-4}$ mmols) it was filled to the 10-mL mark with isopropyl alcohol:water (1:1, V/V). After the solution was vigorously stirred on a vortex mixer it was transferred, via pipette, to a 50-mL, cone-shaped round bottom flask and the flask was sealed with a rubber septum; it was deoxygenated with argon for 30 minutes. The monomeric solution was taken-up by syringe and the needle was capped with a rubber stopper. It was then transferred to an argon-filled glove box along with the polymerization chamber*. The syringe was attached to the polymerization chamber and the solution was inserted into the cell, under argon, to fill the entire cavity. The chamber was sealed with TEFLON® plugs and wrapped in two ZIPLOC® freezer bags. The entire unit was submerged in a 40° C. water-bath and heated for 12 hrs. The polymerization chamber was removed from the bath and the bags, and subsequently disassembled to afford a thin green polymeric film. The polymeric film was placed in a pH 8 NaOH solution for 12 hours, then leached and stored in pH 7.4 phosphate buffer. This product was used in Example 22.

* The polymerization chamber was comprised of (1) An IR cell-holder: two stainless steel plates fashioned to contain the cell and the luer ports; (2) A Cell: two glass plates containing a TEFLON® 0.02" spacer in between, with holes drilled through the top plate and spacer; and (3) A Gasket: a precision-cut rubber spacer used to the seal the cell to the cell-holder.

EXAMPLE 17

Fluorescence Spectroscopy Analysis of 4,4'-N,N'-bis(benzyl-3-boronic Acid)-bipyridinium Dibromide with N,N',N"-tris-(1-aminoethyl-2-polyethylene Glycol (n~125) Methoxy-8-hydroxypyrene-1,3 6-tris-sulfonamide (HPTS-PEG)

A stock solution of HPTS-PEG (10 mL, 5×$10^{-5}$ M) was prepared in a 10-mL volumetric flask with pH 7.4 phosphate buffer (0.1 ionic strength). Similarly, a m-BBV solution (25 mL, 0.0025 M) was prepared. Seven different solutions containing HPTS-PEG and m-BBV were then prepared in pH 7.4 phosphate buffer as described below in Table 2.

TABLE 2

| Volume HPTS-PEG standard (mL) | Volume m-BBV standard (mL) | Volume buffer (mL) | Final [HPTS-PEG] (M) | Final [m-BBV] (M) |
|---|---|---|---|---|
| 1 | 0.00 | 4.00 | 1.00E−05 | 0.00E+00 |
| 1 | 0.20 | 3.80 | 1.00E−05 | 1.00E−04 |
| 1 | 0.30 | 3.70 | 1.00E−05 | 1.50E−04 |
| 1 | 0.50 | 3.50 | 1.00E−05 | 2.50E−04 |
| 1 | 1.00 | 3.00 | 1.00E−05 | 5.00E−04 |
| 1 | 1.50 | 2.50 | 1.00E−05 | 7.50E−04 |
| 1 | 2.00 | 2.00 | 1.00E−05 | 1.00E−03 |

Each sample was then analyzed on the Perkin-Elmer LS50-B luminescence spectrometer. The instrumental settings were:

Excitation Wavelength—473 nm

Emission Wavelength Range—480–630 nm

Excitation Slit Width—0 nm (Instrumental dependent minimum)

Emission Slit Width—0 nm (Instrumental dependent minimum)

Optical filter—none

Scan Speed—100 nm/sec

The instrumental settings (slit widths, scan speed, optical filters, excitation wavelength, emission wavelength range) were held constant throughout the series analysis. The emission fluorescence intensity was then quantified by integration (the trapezoidal rule approximation method) of the fluorescence intensity curve between 480 and 630 nm. The relative integrated values, were then used to construct a calibration curve: plotting $F_o/F$ vs. m-BBV concentration (M), where $F_0$ is the integrated fluorescence intensity of the first sample in Table 2 containing 0 M m-BBV. The apparent Stem-Volmer quenching constant was determined to be 520 $M^{-1}$ (see FIG. 7).

EXAMPLE 18

Glucose Sensing Ability of 4,4'-N,N'-bis(benzyl-3-boronic Acid)-bipyridinium dibromide (M-BBV) with N,N',N"-tris-(1-aminoethyl-2-polyethylene Glycol(n~125)-methoxy 8-hydroxypyrene-1,3,6-tris-sulfonamide (HPTS-PEG) Analyzed by Fluorescence Spectroscopy A stock solution of HPTS-PEG (10 mL, 5×10⁻⁵ M) was prepared in a 10-mL volumetric flask with pH 7.4 phosphate buffer (0.1 ionic strength). Similarly, a m-BBV solution (25 mL, 0.0025 M) and a-D-Glucose (10 mL, 0.250 M) solution were prepared. Seven different solutions containing HPTS-PEG, m-BBV, and α-D-Glucose were then prepared in pH 7.4 phosphate buffer as described below in Table 3:

TABLE 3

| Volume HPTS-PEG stock (mL) | Volume m-BBV stock (mL) | Volume Glucose stock (mL) | Volume buffer (mL) | Final (HPTS-PEG) (M) | Final (m-BBV) (M) | Final (Glucose) (mg/dL) |
|---|---|---|---|---|---|---|
| 1 | 2 | 0 | 2 | 1.00E−05 | 1.00E−03 | 0.00 |
| 1 | 2 | 0.02 | 1.98 | 1.00E−05 | 1.00E−03 | 18.02 |
| 1 | 2 | 0.04 | 1.96 | 1.00E−05 | 1.00E−03 | 36.03 |
| 1 | 2 | 0.2 | 1.8 | 1.00E−05 | 1.00E−03 | 180.16 |
| 1 | 2 | 0.4 | 1.6 | 1.00E−05 | 1.00E−03 | 360.32 |
| 1 | 2 | 1 | 1 | 1.00E−05 | 1.00E−03 | 900.80 |
| 1 | 2 | 2 | 0 | 1.00E−05 | 1.00E−03 | 1801.60 |

The pH of each sample was independently determined using a pH meter to assure that the pH was constant throughout the series to within ±0.02 pH units.

Each sample was then analyzed on the Perkin-Elmer LS50-B luminescence spectrometer. The instrumental settings were:

Excitation Wavelength—473 nm

Emission Wavelength Range—480–630 nm

Excitation Slit Width—0 nm (Instrumental dependent minimum)

Emission Slit Width—0 nm (Instrumental dependent minimum)

Optical filter—none

Scan Speed—100 nm/sec

The instrumental settings (slit widths, scan speed, optical filters, excitation wavelength, emission wavelength range) were held constant throughout the series analysis. The emission fluorescence intensity was then quantified by integration (the trapezoidal rule approximation method) of the fluorescence intensity curve between 480 and 630 nm. The relative integrated values, were then used to construct a calibration curve: plotting F/Fo vs. glucose concentration (mg/dL), where $F_o$ is the integrated fluorescence intensity of the first sample in Table 3 containing 0 mg/dL glucose.

EXAMPLE 19

Comparison of Glucose Sensitivity of Benzyl Viologen vs. 4,4'-N,N'-bis(benzyl-3-boronic Acid)-bipyridinium Dibromide with HPTS-PEG The glucose sensing ability of benzyl viologen was compared to that of 4,4'-N,N'-bis(benzyl-3-boronic acid)-bipyridinium dibromide in the presence of HPTS-PEG dye. The apparent Stern-Volmer quenching constant for benzyl viologen with HPTS-PEG was determined as described in Procedure A, and found to be 559 $M^{-1}$. The glucose sensitivity of benzyl viologen in the presence of BPTS-PEG was determined as in example 18. The signal from the benzyl viologen/HPTS-PEG solution did not respond to changes in glucose concentration. The glucose sensitivity of 4,4'-N,N'-bis(benzyl-3-boronic acid)-bipyridinium dibromide, as found in Example 18, is shown in FIG. 5 together with the glucose sensitivity of benzyl viologen.

EXAMPLE 20

Fluorescence Spectroscopy Analysis of Water Soluble Copolymer of 4-N-(benzyl-3-boronic Acid)-4'-N'-(benzyl-4-ethenyl)-dipyridinium Bromide Chloride (M-SBBV)

A stock solution of water-soluble poly m-SBBV (50 mL, 2.5 mM) was prepared in pH 7.4 phoshate buffer and pH balanced (±0.02 pH units) with NaOH solution. Six different solutions of poly m-SBBV (the analyte, 0, 0.10, 0.15, 0.25, 0.50, 0.75, 1.0 mM) containing HPTS-PEG (dye, $1 \times 10^{-5}$ M) were then prepared and analyzed on the spectrofluorimeter. The analyte/dye solutions were contained in a standard 10-mm path length, quartz cuvet, and the spectrofluorimeter was set to an excitation and emission frequency of 473 and 533, respectively. The excitation and emission slit widths were set to 0 nm. After the fluorescence spectra were obtained for the solutions mentioned above, additional spectra of the analyte/dye solutions were obtained in the presence and absence of glucose and fructose. The apparent differences in spectra were quantified as areas under the curve. The difference in areas was then determined to be representative of the polymer response to glucose or fructose, e.g., in the absence of glucose or fructose the representative area under the curve was determined to be 26479.45. Upon addition of different concentrations of glucose, the areas changed accordingly as indicated in Table 4.

TABLE 4

Change in Fluorescence Intensity of 1.0 mM poly m-SBBV/HPTS-PEG Solutions After Addition of Glucose; Represented as the Area Under the Curve

| (Glucose) (mg/dl) | Area Under Curve |
|---|---|
| 0 | 26479.45 |
| 18 | 26934.93 |
| 36 | 27163.92 |
| 180 | 27988.86 |
| 360 | 28221.08 |
| 900 | 28810.57 |
| 1800 | 29434.23 |

Thus, the fluorescence intensity increased by 11% upon addition of 1800 mg/dl of glucose and 14.6% upon addition of 1800 mg/dl of fructose.

EXAMPLE 21

Fluorescence Spectroscopy Analysis of IPN: Copolymer of 4-N-(benzyl-3-boronic Acid)-4'-N'-(benzyl-4-ethenyl)-dipyridinium Bromide Chloride (M-SBBV) Using Dispersed HPTS-MA Hydrogel A 10-mm path length, 5-mL disposable polystyrene cuvet was modified using a hot metal rod to melt a 3.9 mm diameter hole into the bottom center of the cuvet. While the plastic was still malleable the threads of a 10–32 standard thread, ⅛" I.D. hose end adapter were screwed into the plastic. The plastic was allowed to cool and the adapter was unscrewed. TEFLON® thread tape was applied to the threads. The adapter was then refit into the cuvet. A disposable polyethylene cuvet cap was modified similarly by puncturing a hole in the center of the cap and threading into the hole an identical 10–32 standard thread to ⅛" I.D. hose adapter. A thin sheet of clear plastic was then cut into a 35×9 mm rectangle and a window 6×15 mm was cut out of the center. Two pressure fittings were constructed from the plunger of a Tuberculin Monoject 1-mL syringe. They were used to put pressure on the plastic mask to hold the polymer in place within the cuvet. The round thumb button of the plunger was used as the pressure plate and was removed from the shaft such that the height of the bottom of the plate to the top of the shaft was 9 mm. The flow-through-cell was then assembled such that the polymer film was in the center of the cuvet and the clear plastic mask directly over it, effectively framing the film with its window. The pressure fittings were then put in place using tweezers, one at the bottom of the cell and one at the top, oriented with the broad base against the plastic mask. The out side wall of the cuvet cap, which sits inside the cuvet, was then coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face first in the front surface adapter). ⅛" TYGON® PTFE tubing was connected to the hose adapters of the flow-through-cell. The orientation of the front surface adapter was optimized so that the emission detector was sensing only the surface of the polymer. A peristaltic pump was used to circulate pH 7.4 phosphate buffer (ionic strength 0.1) through the cell at a rate of 30 mL per minute. The time drive function of the Perkin-Elmer LS50B software was used to acquire fluorescence intensity readings every ten seconds with an integration time of two seconds. The excitation frequency was set at 475 nm and the emission frequency was set at 536 nm. The excitation and emission slit widths were set at 15 nm and 20 nm, respectively. A base line value of 249 (fluorescence intensity) was established with buffer solution. The peristaltic pump was stopped and the pumping solution was changed to 1800 mg/dl glucose in pH 7.4 phosphate buffer. The fluorescence intensity increased 25 units to a value of 274, corresponding to a 10% signal increase (S/N ratio=43). After switching back to buffer the signal approached the expected baseline value of 249.

EXAMPLE 22

Fluorescence Spectroscopy Analysis of Two Component System: Thin Film Copolymer Hydrogel of 4-N-(benzyl-3-boronic Acid)-4'-N'-(benzyl-4-ethenyl)-dipyridinium Bromide Chloride (M-SBBV) Using Acetoxy-HPTS-MA A 10-mm path length, 5-mL disposable polystyrene cuvet was modified using a hot metal rod to melt a 3.9 mm diameter hole into the bottom center of the cuvet. While the plastic was still malleable the threads of a 10–32 standard thread, ⅛" I.D. hose end adapter were screwed into the plastic. The plastic was allowed to cool and the adapter was unscrewed. TEFLON® thread tape was applied to the threads. The adapter was then refit into the cuvet. A disposable polyethylene cuvet cap was modified similarly by puncturing a hole in the center of the cap and threading into the hole an identical 10–32 standard thread to ⅛" I.D. hose adapter. A thin sheet of clear plastic was then cut-into a 35×9 mm rectangle and a window 6×15 mm was cut out of the center. Two pressure fittings were constructed from the plunger of a Tuberculin Monoject 1-mL syringe. They were used to put pressure on the plastic mask to hold the polymer in place within the cuvet. The round thumb button of the plunger was used as the pressure plate and was removed from the shaft such that the height of the bottom of the plate to the top of the shaft was 9 mm. The flow-through-cell was then assembled such that the polymer film was in the center of the cuvet and the clear plastic mask directly over it, effectively framing the film with its window. The pressure fittings were then put in place using tweezers, one at the bottom of the cell and one at the top, oriented with the broad base against the plastic mask. The out side wall of the cuvet cap, which sits inside the cuvet, was then coated with vacuum grease and inserted into the cuvet to seal the cell. The cell was placed into a Perkin-Elmer LS50B spectrophotometer equipped with a front surface adapter. The cell was oriented so that its side, touching the polymer, was facing the excitation beam of the instrument (face first in the front surface adapter). ⅛" TYGON® PTFE tubing was connected to the hose adapters of the flow-through-cell. The orientation of the front surface adapter was optimized so that the emission detector was sensing only the surface of the polymer. A peristaltic pump was used to circulate pH 7.4 phosphate buffer (ionic strength 0.1) through the cell at a rate of 30 mL per minute. The time drive function of the Perkin-Elmer LS50B software was used to acquire fluorescence intensity readings every ten sec with an integration time of 2 sec. The excitation frequency was set at 475 nm and the emission frequency was set at 536 nm. The excitation and emission slit widths were set at 7 nm. A base line value of 490 (fluorescence intensity) was established with buffer solution. The peristaltic pump was stopped and the pumping solution was changed to 400 mg/dl glucose in pH 7.4 phosphate buffer. The fluorescence intensity increased nine units to a value of 499, corresponding to a 1.5% signal increase (S/N ratio=6.5). The process of switching solutions was repeated. The buffer gave an expected base line of 490. After changing to 1800 mg/dl glucose in pH 7.4-phosphate buffer the fluorescence intensity rose 35 units to a value of 525, corresponding to a 7.6% signal increase (S/N=15.0). Finally, the base line dropped to the expected value of 490 when buffer was pumped through the system.

EXAMPLE 23

Fluorescence Spectrophotometric Determination of Glucose Concentration in an Aqueous Sample with 4,4'-N,N'-bis(benzyl-3-boronic Acid)-bipyridinium Dibromide (M-BBV) and N,N',N"-tris-(1-aminoethyl-2-polyethylene Glycol(n~125)-methoxy-8-hydroxypyrene-1,3,6-tris-sulfonamide (HPTS-PEG)

A stock solution of HPTS-PEG (10 ml, 5×10–5 M) is prepared in a 10-mL volumetric flask with pH 7.4 phosphate buffer (0.1 ionic strength). Similarly, a m-BBV solution (25 mL, 0.0025 M) and ∝-D-Glucose (10 mL, 0.250 M) solution are prepared. Seven different solutions containing HPTS-PEG, m-BBV, and ∝-D-Glucose are then prepare in pH 7.4 phosphate buffer as described below in Table 5.

TABLE 5

| Volume HPTS-PEG stock (mL) | Volume m-BBV stock (mL) | Volume Glucose stock (mL) | Volume buffer (mL) | Final [HPTS-PEG] (M) | Final [m-BBV] (M) | Final [Glucose] (mg/dL) |
|---|---|---|---|---|---|---|
| 1 | 2 | 0 | 2 | 1.00E–05 | 1.00E–03 | 0.00 |
| 1 | 2 | 0.02 | 1.98 | 1.00E–05 | 1.00E–03 | 18.02 |
| 1 | 2 | 0.04 | 1.96 | 1.00E–05 | 1.00E–03 | 36.03 |
| 1 | 2 | 0.2 | 1.8 | 1.00E–05 | 1.00E–03 | 180.16 |
| 1 | 2 | 0.4 | 1.6 | 1.00E–05 | 1.00E–03 | 360.32 |
| 1 | 2 | 1 | 1 | 1.00E–05 | 1.00E–03 | 900.80 |
| 1 | 2 | 2 | 0 | 1.00E–05 | 1.00E–03 | 1801.60 |

The pH of each sample is independently determined using a pH meter to assure that the pH is constant throughout the series to within ±0.02 pH units.

Each sample is then analyzed on a Perkin-Elmer LS50-B luminescence spectrometer. The instrumental settings are as follows:

Excitation Wavelength—473 nm
Emission Wavelength Range—480–630 nm
Excitation Slit Width—0 nm (Instrumental dependent minimum)
Emission Slit Width—0 nm (Instrumental dependent minimum)
Optical filter—none
Scan Speed—100 nm/sec The instrumental settings (slit widths, scan speed, optical filters, excitation wavelength, emission wavelength range) are held constant throughout the series analysis. The fluorescence emission intensity is then quantified by integration (using the trapezoidal rule approximation method) of the fluorescence intensity curve between 480 and 630 nm. A calibration curve is constructed plotting the quantified fluorescence emission intensity values vs. the corresponding glucose concentration (mg/dL). Two mL of an aqueous glucose solution of unknown concentration are placed in a 5-mL volumetric flask to which is added 1 mL of HPTS-PEG stock solution and 2 mL of m-BBV stock solution. The sample is mixed, placed into an appropriate cuvet and the fluorescence emission intensity of the sample is analyzed as previously described. The fluorescence emission intensity is then quantified by integration (using the trapezoidal rule approximation method) of the fluorescence emission intensity curve between 480 and 630 nm. The glucose concentration for the unknown can be determined by comparison of the quantified value for the fluorescence emission intensity of the sample of unknown glucose concentration to the calibration curve on the y-axis and reading the corresponding glucose concentration on the x-axis. The glucose concentration read off the calibration chart is then adjusted for the 5/2 dilution factor to determine the glucose concentration of the unknown sample.

EXAMPLE 24

Fluorescence Spectrophotometric Determination of Glucose Concentration in an Aqueous Sample with the Thin Film Copolymerization of 4-N-(benzyl-3-boronic Acid)-4'-N'--(benzyl-4ethenyl)-dipyridinium Bromide Chloride Using HPTS-PEG (Semi-IPN Thin Film)

The thin film copolymer is prepared as described in Example 12 and mounted in the fluorescence spectrometer as described in Example 13. Seven 100 ml stock solutions of ∝-D-Glucose (0, 18, 36, 180, 360, 900, and 1800 mL/dL) are then prepared in pH 7.4 phosphate buffer. The 7 solutions are sequentially circulated through the flow through cell and the fluorescence emission intensities analyzed as described in Example 13. In each case the fluorescence emission intensity is allowed to stabilize prior to changing solutions. A calibration curve is constructed plotting the stabilized fluorescence intensity values vs. the corresponding glucose concentrations. The pH value of an aqueous glucose sample of unknown concentration is determined with a pH meter and adjusted to pH 7.4±0.02 with concentrated acid or base. The unknown sample is circulated through the flow through cell and the fluorescence emission intensity observed until it stabilizes. The glucose concentration for the unknown sample is circulated through the flow through cell and the fluorescence emission intensity observed until it stabilizes. The glucose concentration for the unknown can be determined by comparison of its quantified value for the stable fluorescence emission intensity to the calibration curve on the y-axis and reading the corresponding glucose concentration on the x-axis. The final determined glucose concentration for the unknown sample is adjusted for any dilution factor caused by adjusting the pH of the sample.

While only a few embodiments of the invention have been shown and described herein, it will become apparent to those skilled in the art that various modifications and changes can be made in a glucose sensor and its components including the fluorophore dye, quencher and optional polymer matrix for monitoring polyhydroxyl-containing organic analytes, primarily for in vitro glucose monitoring, without departing from the spirit and scope of the present invention. All such modifications and changes coming within the scope of the appended claims are intended to be carried out thereby.

We claim:

1. An optical method for the in vitro detection between about 300 and 800 nm of polyhydroxyl-substituted organic molecules as the analyte in an analyte solution selected from aqueous liquid, an organic liquid or combinations thereof at pH of about 5 to 9, which method comprises:
  A. obtaining a flurorophore dye D, which is compatible with the analyte solution, wherein D is selected from:
    (a) $D^1$ which is a fluorophore dye having the properties of:
      i. A fluorophore,
      ii. An excitation in the range greater than 300 nm and less than 800 nm,
      iii. Resistant to photobleaching under the conditions of analysis,
      iv. A Stokes shift of about or greater than 30 nm,
      v. Compatibility with said analyte solution, and wherein said
      vi. Dye $D^1$ is quenched by methyl viologen to produce an experimentally determined apparent Stern-Volmer quenching constant (Ksv) greater than or equal to 50,
        wherein the fluorophore dye $D^1$ is a discrete soluble compound, or is a pendant group or chain unit in a water-soluble or dispersible or organic liquid soluble or dispersible polymer, and said polymer optionally is non-covalently associated with an insoluble polymer matrix $M^1$ and is physically immobilized within said polymer matrix $M^1$; and
        wherein said polymer matrix $M^1$ is permeable to or in contact with said analyte solution;
    (b) $D^2$ is a fluorophore dye having the properties of:
      i. A fluorophore,
      ii. An excitation in the range greater than 300 nm and less than 800,
      iii. A Stokes shift of about or greater than 30 nm,
      iv. Resident to photobleaching under the conditions of analysis,
      v. Compatibility in the analyte solution, and wherein said
      vi. Dye $D^2$ is quenched by methyl viologen to produce an apparent Stern-Volmer quenching constant (Ksv) greater than or equal to 50, wherein $D^2$ is covalently bonded to an insoluble polymer matrix wherein said polymer matrix $M^1$ is permeable to or in contact with said analyte; wherein said fluorophore dye $D^2$ is a part of the structure:

$M^1$—$L^1$—$D^2$ wherein:
      $M^1$ is said polymer matrix,
      $L^1$ is a hydrolytically stable covalent linking group selected from the group consisting of a direct bond, lower alkylene having 1 to 4 carbon atoms, sulfonamide, amide, ester, ether, sulfide, sulfone, phenylene, urethane, urea, thiourea and amine, and $D^2$ is said fluorophore dye which is covalently bonded to said polymer matrix $M^1$, with the proviso that $D^2$ as a poly-functional moiety is covalently bonded to said matrix $M^1$ at one, two or three sites;
  B. Combining with a analyte solution-compatible boronic acid-containing quencher molecule Q, wherein Q is a conjugated aromatic nitrogen-containing heterocyclic bis-onium salt selected from:
    (i) $Q^1$ which is a discrete soluble compound or is a pendant group or chain unit in a water soluble or dispersible polymer or organic liquid soluble or dispersible polymer and said polymer is optionally non-covalently associated with an optional polymer matrix $M^1$ when present and immobilized within said polymer matrix $M^1$, wherein $Q^1$ is a compound having the properties of:
      compatibility in said analyte solution,
      produces a detectable change in the emission of the dye in the presence of said analyte, or
    (ii) $Q^2$ which is a structure having the properties of:
      compatibility in said analyte solution produces a detectable change in the emission of the dye in the presence of said analyte, and
        wherein $Q^2$ is covalently bonded by linking group $L^2$ to $M^1$ or to a second insoluble polymer matrix $M^2$ producing $M^2$—$L^2$—$Q^2$ wherein $L^2$ is selected from the group consisting of a direct bond, a lower alkylene having 1 to 4 carbon atoms, sulfonamide, amide, ester, ether, sulfide, sulfone, phenylene, urethane, urea, thiourea and amine, with the proviso that $Q^2$ as a poly-functional moiety is covalently bonded to said matrix $M^1$ or $M^2$ at one or two sites;
        wherein said quencher $Q^1$ or $Q^2$ is mixed at a molecular level with said fluorophore dye $D^1$ or $D^2$, and
  C. contacting a test solution of analyte, a dye and a quencher in vitro with an excitation light source coupled with a detector;
  D. producing a detectable and quantifiable signal in the range of about 300 to 800 nm; and
  E. determining the concentration of said polyhydroxyl-substituted analyte in said aqueous liquid, organic liquid or combinations thereof.

2. The method of claim 1 wherein the Dye $D^1$ is selected from the group consisting of
pyranine;
pyranine derivatives having the structure of:

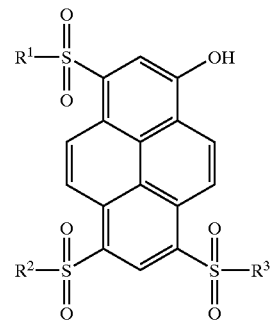

where
R$^1$, R$^2$ and R$^3$ are same or different and wherein R$^1$, R$^2$ and R$^3$ are each selected from:
—OH, —N(R$^4$)R$^5$, wherein R$^4$ is selected from —H, —CH$_3$, and —CH$_2$CH$_2$OH, and
R$^5$ is selected from —CH$_2$—CH$_2$(—O—CH$_2$—CH$_2$)$_n$—X$^1$ or R$^6$X$^1$, wherein X$^1$ is selected from —OH, —OCH$_3$, —CO$_2$H, —CONH$_2$, —SO$_3$H, or —NH$_2$, and R$^6$ is a lower alkylene or hydroxyalkylene having 2 to 6 carbon atoms;
n is about 2 to 10,000, coumarin 343; eosin Y; fluorescein; 4,4-difluoro-1,3,5,7,8-pentamethyl-4-bora-3a,4a-diaza-s-indacene-2,6-disulfonic acid, disodium salt (Molecular Probes D-3238); Lucifer Yellow Iodoacetamide dipotassium salt (Molecular Probes L-1338); and fluorescein-5-(and-6)-sulfonic acid, trisodium salt (Molecular Probes F-1130).

3. The method of claim 1 wherein the Dye D$^2$ is prepared from:

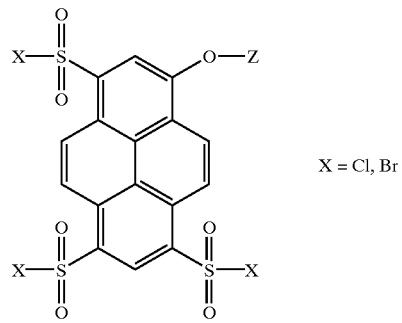

X = Cl, Br or from a dye monomer selected from the group consisting of:

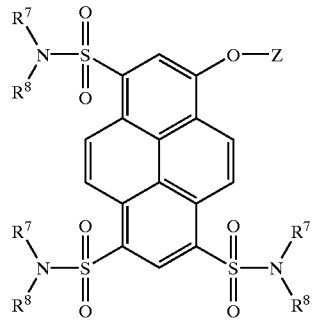

where
R$^7$=—H, —CH$_2$—CH=CH$_2$ and when R$^7$=—H then R$^8$ is selected from —R$^9$—NH—(C=O)—(C=CH$_2$)—R$^{10}$, —R$^9$—O—(C=O)—(C=CH$_2$)—R$^{11}$, or —CH$_2$—C$_6$H$_4$—CH=CH$_2$, and where R$^9$ is lower alkylene having 2–6 carbon atoms and
where R$^{10}$ and R$^{11}$ are each —H, —CH$_3$ and when R$^7$ is —CH$_2$—CH=CH$_2$ then R$^8$ is —H, —CH$_2$—CH=CH$_2$,
and Z is a blocking group that can be removed by hydrolysis selected from:

—(C=O)—R$^{12}$—Y where R$^{12}$ is a lower alkylene having 1 to 4 carbon atoms and Y is selected from —H, —OH, —CO$_2$H, —SO$_3$H, —(C=O)—NH—R$^{13}$, or —CO$_2$—R$^{13}$, where R$^{13}$ is a lower alkylene having 1 to 4 carbon atoms.

4. The method of claim 1 wherein Q$^1$ is selected from the group consisting of nitrogen containing conjugated heterocyclic aromatic bis-onium salts wherein the heterocyclic aromatic core is selected from the isomers of dipyridyl, phenanthroline, dipyridylethylene, dipyridylphenylene, and diazafluorene wherein the two nitrogen atoms are each in different aromatic rings and the nitrogen atoms are in all positions of the ring capable of forming an onium salt, and at least one of the substituents on the nitrogens is selected from ortho-, meta-, or para-benzyl boronic acids, preferably where both substituents are benzyl boronic acids.

5. The method of claim 1 wherein the quencher Q$^1$ is selected from the group consisting of:

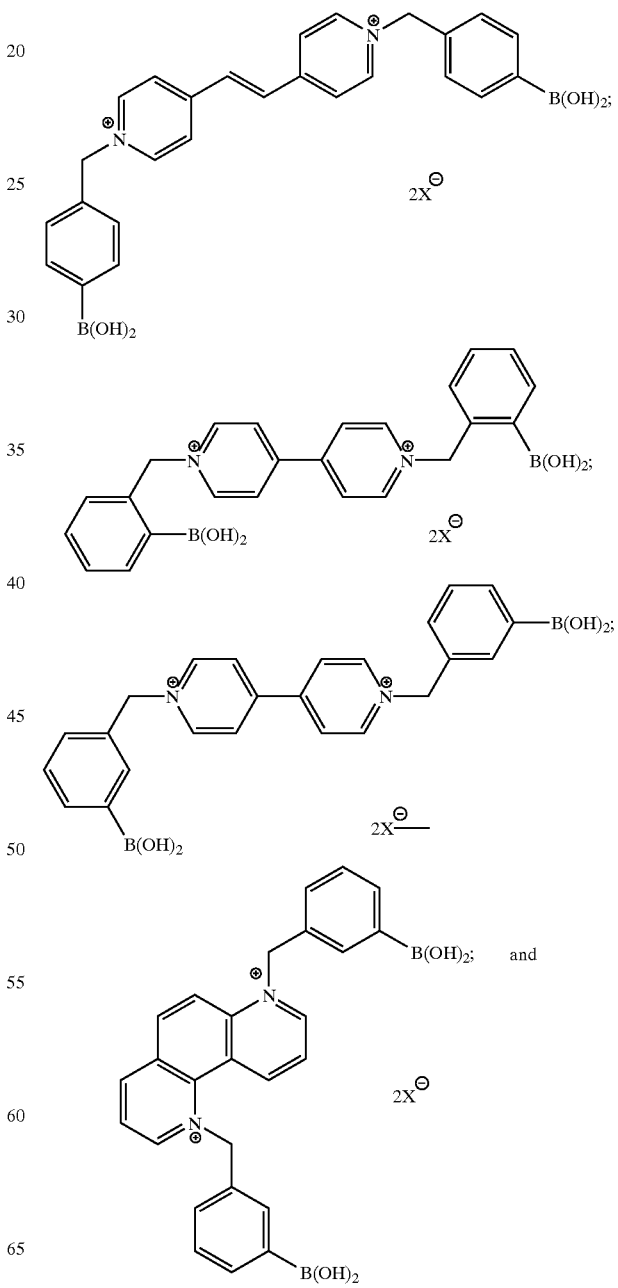

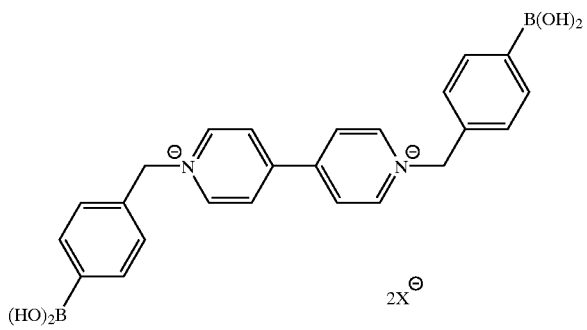

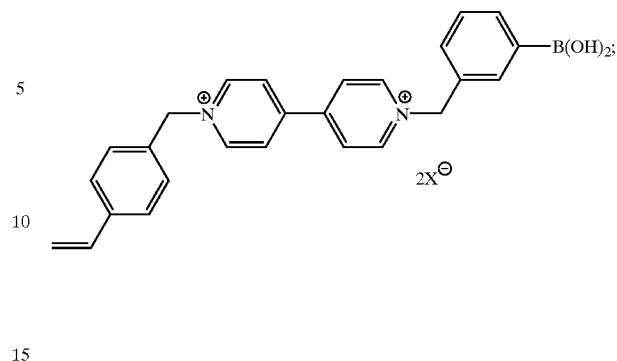

wherein X is chloro or bromo.

6. A method of claim 1 where the quenchers $Q^1$ and $Q^2$ are derived from precursors selected from:

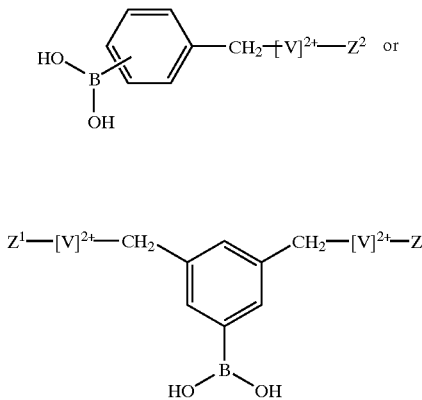

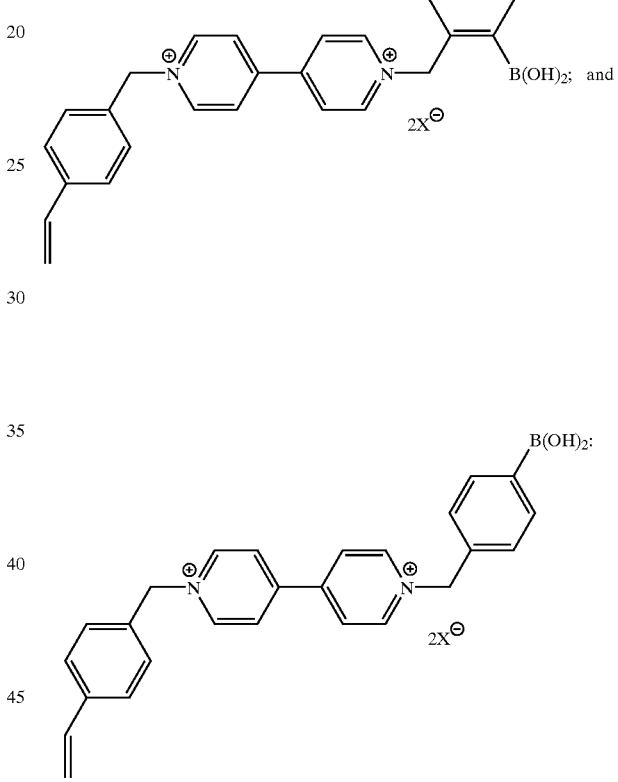

wherein X is chloride, bromide or combinations thereof.

8. The method of claim 1 wherein in substep A, the fluorophore is $D^1$.

9. The method of claim 1 wherein in substep A, the fluorophore is $D^2$.

10. The method of claim 1 wherein in substep B, quencher Q is $Q^1$.

11. The method of claim 1 wherein in substep B, quencher Q is $Q^2$.

12. The method of claim 1 wherein in substep A, D is $D^1$ and in substep B, Q is $Q^1$.

13. The method of claim 1 wherein in substep A the fluorophore $D^1$ is selected from pyranine derivatives having the structure of:

wherein $(V)^{2+}$ is a nitrogen containing conjugated heterocyclic aromatic group selected from isomers of dipyridyls, dipyridyl ethylenes, dipyridyl phenylenes, phenanthrolines, or diazafluorenes wherein the two nitrogen atoms are each in a different aromatic ring and the nitrogen atoms are in all positions of the ring capable of forming an onium salt; and $Z^1$ or $Z^2$ each are either a polymerizable ethylenically unsaturated group selected from:

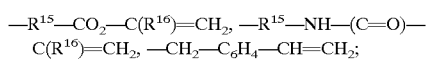

$R^{15}$ is a lower alkylene or hydroxyalkylene of 2 to 6 carbon atoms;

$R^{16}$=—H, —$CH_3$ or a coupling group selected from —$R^{17}$—$Z^3$, wherein $R^{17}$ is —$CH_2C_6H_4$— or alkylene of 2 to 6 carbon atoms, and $Z^3$ is selected from —OH, —SH, —$CO_2H$, or —$NH_2$.

7. The method of claim 1 wherein the quenchers $Q^1$ and $Q^2$ are prepared from a quencher precursor selected from the group consisting of:

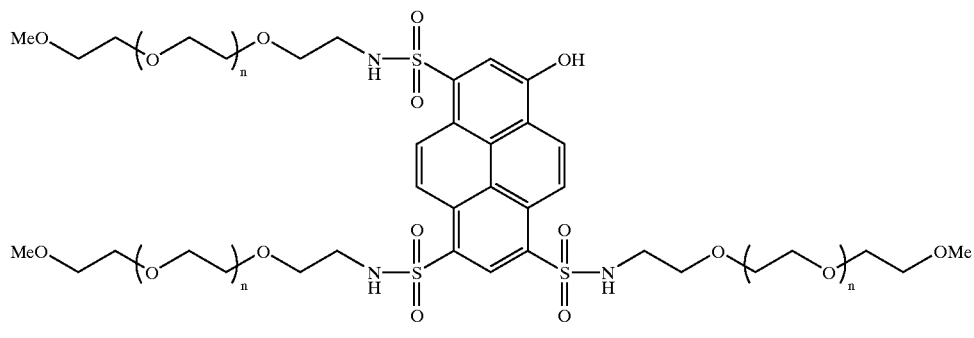
wherein n is between about 2 and 200.
14. The method of claim 13 wherein in substep A the precursor to dye $D^2$ is:
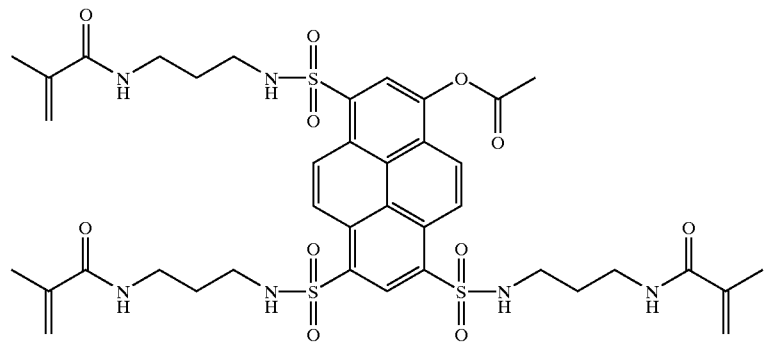
and in step B the quencher is selected from the group consisting of
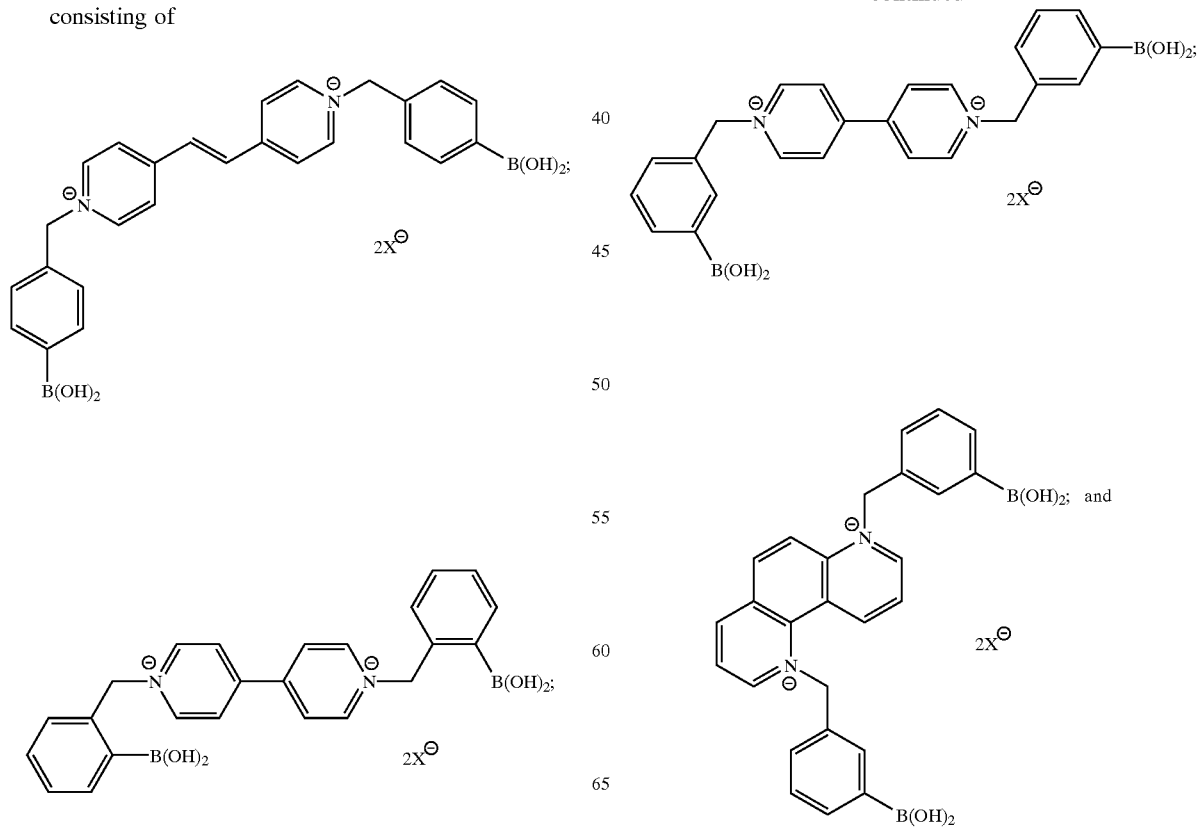

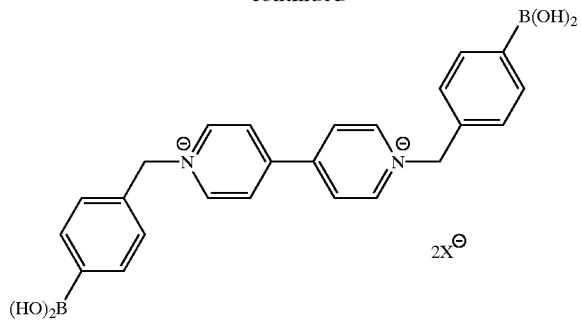

wherein X is bromide, chloride or combinations thereof.

15. The method of claim 1 wherein the polyhydroxyl-substituted organic molecules are sugars selected from glucose or fructose.

16. The method of claim 15 wherein the Dye $D^1$ is selected from the group consisting of

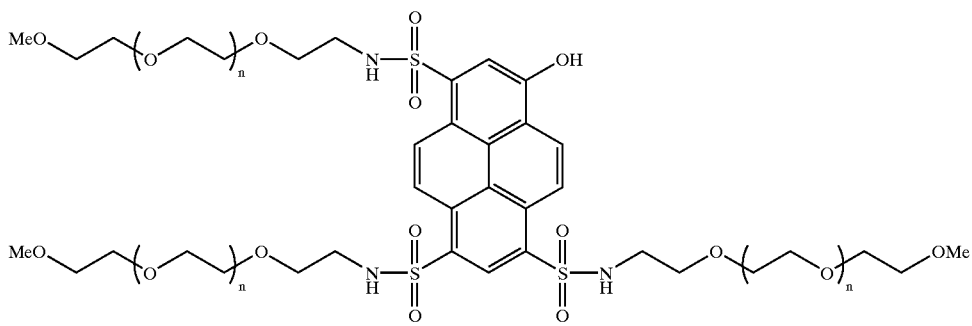

wherein n is about 2 to 200.

17. The method of claim 15 wherein the quencher $Q^1$ is selected from the group consisting of

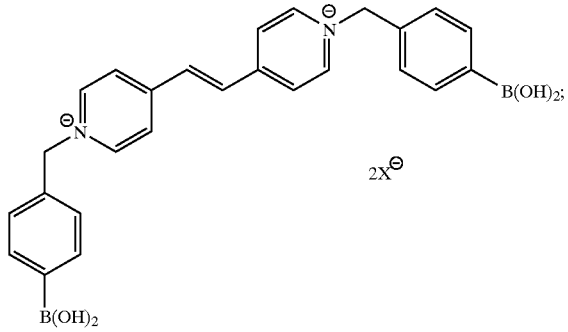

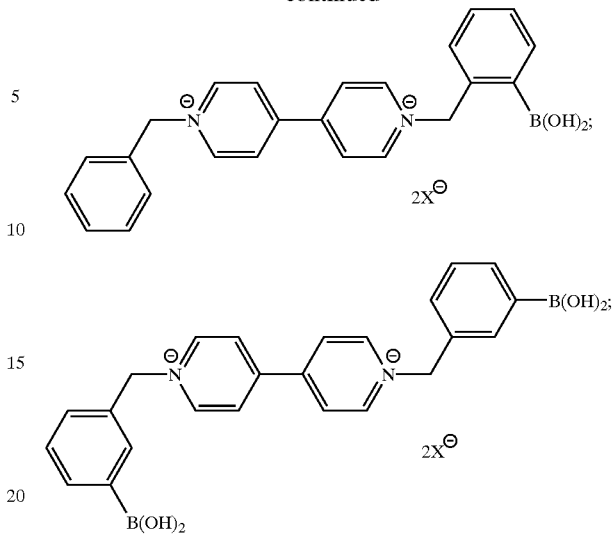

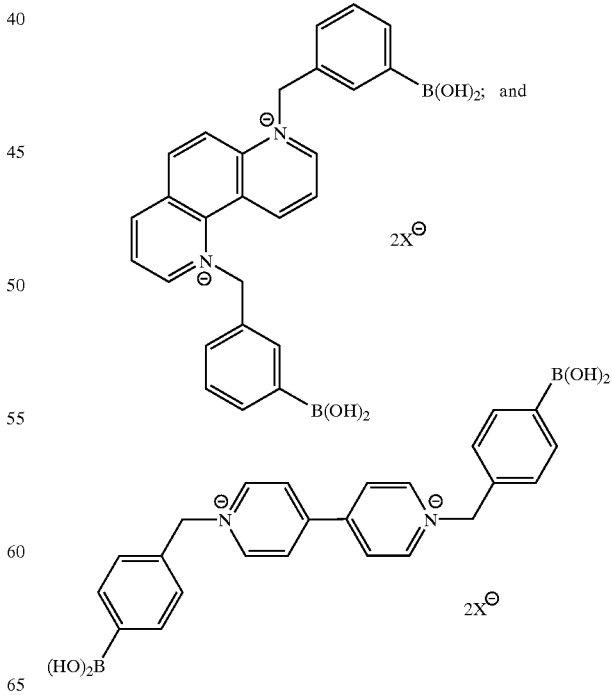

wherein X is bromide, chloride, or combinations thereof.

18. An optical device for the in vitro detection between about 300 and 800 nm of polyhydroxyl-substituted organic molecules as the analyte in an analyte solution selected from aqueous liquid, an organic liquid or combinations thereof at pH of about 5 to 9, which device comprises:

a fluorophore Dye D, a boronic acid—containing quencher molecule Q, a polymer matrix M or $M^1$, an excitation light source, and a detector, wherein A. said flurorophore dye D, which is compatible with the analyte solution, wherein D is selected from:
  (a) $D^1$ which is a fluorophore dye having the properties of:
    i. A fluorophore,
    ii. An excitation in the range greater than 300 nm and less than 800 nm,
    iii. Resistant to photobleaching under the conditions of analysis,
    iv. A Stokes shift of about or greater than 30 nm,
    v. Compatibility with said analyte solution, and wherein said
    vi. Dye $D^1$ is quenched by methyl viologen to produce an experimentally determined apparent Stern-Volmer quenching constant (Ksv) greater than or equal to 50, wherein the fluorophore dye $D^1$ is a discrete soluble compound, or is a pendant group or chain unit in a water-soluble or dispersible or organic liquid solid or dispersible polymer, and said polymer optionally is non-covalently associated with an insoluble polymer matrix $M^1$ and is physically immobilized within said polymer matrix $M^1$; and
      wherein said polymer matrix $M^1$ is permeable to or in contact with said analyte solution;
  (b) $D^2$ is a fluorophore dye having the properties of:
    i. A fluorophore,
    ii. An excitation in the range greater than 300 nm and less than 800,
    iii. A Stokes shift of about or greater than 30 nm,
    iv. Resident to photobleaching under the conditions of analysis,
    v. Compatibility in the analyte solution, and wherein said
    vi. Dye $D^2$ is quenched by methyl viologen to produce an apparent Stem-Volmer quenching constant (Ksv) greater than or equal to 50, wherein $D^2$ is covalently bonded to an insoluble polymer matrix wherein said polymer matrix $M^1$ is permeable to or in contact with said analyte;
      wherein said fluorophore dye $D^2$ is a part of the structure:

$$M^1-L^1-D^2$$

wherein:

$M^1$ is said polymer matrix, $L^1$ is a hydrolytically stable covalent linking group selected from the group consisting of a direct bond, lower alkylene having 1 to 4 carbon atoms, sulfonamide, amide, ester, ether, sulfide, sulfone, phenylene, urethane, urea, thiourea and amine, and $D^2$ is said fluorophore dye which is covalently bonded to said polymer matrix $M^1$, with the proviso that $D^2$ as a poly-functional moiety is covalently bonded to said matrix $M^1$ at one, two or three sites;

B. when combined with a analyte solution-compatible boronic acid-containing quencher molecule Q, wherein Q is a conjugated aromatic nitrogen-containing heterocyclic bis-onium salt selected from:
  (i) $Q^1$ which is a discrete soluble compound or is a pendant group or chain unit in a water soluble or dispersible polymer or organic liquid soluble or dispersible polymer and said polymer is optionally non-covalently associated with an optional polymer matrix $M^1$ when present and immobilized within said polymer matrix $M^1$, wherein $Q^1$ is a compound having the properties of:
    compatibility in said analyte solution, produces a detectable change in the emission of the dye in the presence of said analyte, or
  (ii) $Q^2$ which is a structure having the properties of:
    compatibility in said analyte solution produces a detectable change in the emission of the dye in the presence of said analyte, and
      wherein $Q^2$ is covalently bonded by linking group $L^2$ to $M^1$ or to a second insoluble polymer matrix $M^2$ producing $$M^2-L^2-Q^2$$

wherein $L^2$ is selected from the group consisting of a direct bond, a lower alkylene having 1 to 4 carbon atoms, sulfonamide, amide, ester, ether, sulfide, sulfone, phenylene, urethane, urea, thiourea and amine, with the proviso that $Q^2$ as a poly-functional moiety is covalently bonded to said matrix $M^2$ at one or two sites;

wherein said quencher $Q^1$ or $Q^2$ is mixed at a molecular level with said fluorophore dye $D^1$ or $D^2$, and C. contacting within said matrix M or $M^1$ a test solution of analyte, dye and quencher, in vitro with an excitation light source coupled with a detector;

D. producing a detectable and quantifiable signal in the range of about 300 to 800 nm; and thus is E. determined continuously or intermittently the concentration of said polyhydroxyl-substituted analyte in said aqueous liquid, organic liquid or combinations thereof.

* * * * *